United States Patent
Gutierrez et al.

(10) Patent No.: US 10,098,950 B2
(45) Date of Patent: Oct. 16, 2018

(54) PD-1 PEPTIDE INHIBITORS

(71) Applicant: Leidos, Inc., Reston, VA (US)

(72) Inventors: Gabriel M. Gutierrez, Reston, VA (US); Vinayaka Kotraiah, Reston, VA (US); James Pannucci, Reston, VA (US); Ramses Ayala, Reston, VA (US)

(73) Assignee: Leidos, Inc., Reston, VA (US)

( * ) Notice: Subject to any disclaimer, the term of this patent is extended or adjusted under 35 U.S.C. 154(b) by 0 days.

(21) Appl. No.: 15/705,333

(22) Filed: Sep. 15, 2017

(65) Prior Publication Data

US 2018/0071385 A1 Mar. 15, 2018

Related U.S. Application Data

(60) Provisional application No. 62/395,195, filed on Sep. 15, 2016.

(51) Int. Cl.

| | |
|---|---|
| *A61K 6/00* | (2006.01) |
| *A61K 39/00* | (2006.01) |
| *A61K 39/002* | (2006.01) |
| *A61K 39/015* | (2006.01) |
| *A61K 39/395* | (2006.01) |
| *A61K 45/00* | (2006.01) |
| *A61K 45/06* | (2006.01) |
| *C07K 1/00* | (2006.01) |
| *C07K 16/00* | (2006.01) |
| *C07K 16/18* | (2006.01) |
| *C07K 16/20* | (2006.01) |
| *A61K 39/39* | (2006.01) |
| *A61K 38/16* | (2006.01) |
| *A61K 38/10* | (2006.01) |
| *C07K 7/08* | (2006.01) |

(52) U.S. Cl.
CPC .............. *A61K 39/39* (2013.01); *A61K 38/10* (2013.01); *A61K 38/16* (2013.01); *A61K 39/0011* (2013.01); *A61K 39/015* (2013.01); *C07K 7/08* (2013.01); *A61K 2039/55516* (2013.01)

(58) Field of Classification Search
None
See application file for complete search history.

(56) References Cited

U.S. PATENT DOCUMENTS

| | | |
|---|---|---|
| 2002/0111323 A1 | 8/2002 | Martin et al. |
| 2011/0318373 A1 | 12/2011 | Sasikumar et al. |
| 2013/0237580 A1 | 9/2013 | Sasikumar et al. |

FOREIGN PATENT DOCUMENTS

| | | |
|---|---|---|
| WO | 2012168944 A1 | 12/2012 |
| WO | 2013144704 A1 | 10/2013 |
| WO | 2014127917 A1 | 8/2014 |

OTHER PUBLICATIONS

Adams et al., "Big opportunities for small molecules in immuno-oncology," Nature Reviews Drug Discovery Advance Online Publication, Jul. 31, 2016, 20 pages.
Bruno et al., "Basics and recent advances in peptide and protein drug delivery," Ther. Deliv. 4, 1443-67, 2013.
Bu et al., "Learning from PD-1 Resistance: New Combination Strategies," Trends Mol. Med. 22, 448-51, 2016.
Cao, "Advances in Delivering Protein and Peptide Therapeutics," Pharmaceutical Technology 40, 22-24, Nov. 2, 2016.
John et al., "Blockade of PD-1 immunosuppression boosts CAR T-cell therapy," OncoImmunology 2, e26286, 3 pages, 2013.
Chong et al., "PD-1 blockade modulates chimeric antigen receptor (CAR)-modified T cells: refueling the CAR," Blood. 129(8), 1039-41, 2017, published on-line Dec. 28, 2016.
Creative Biolabs User Manual, "TriCo-20TM Phage Display 20-mer Random Peptide Library," 14 pages, Aug. 4, 2009.
Differding, "AUNP-12—A Novel Peptide Therapeutic Targeting PD-1 Immune Checkpoint Pathway for Cancer Immunotherapy—Structure Activity Relationships & Peptide/Peptidomimetic Analogs," available at http://www.differding.com/data/AUNP_12_A_novel_peptide_therapeutic_targeting_PD_1_immune_checkpoint_pathway_for_cancer_immunotherapy.pdf, Feb. 26, 2014.
Duraiswamy et al., "Dual Blockade of PD-1 and CTLA-4 Combined with Tumor Vaccine Effectively Restores T-Cell Rejection Function in Tumors," Cancer Res 73, 3591-603, 2013.
Feridooni et al., "Noninvasive Strategies for Systemic Delivery of Therapeutic Proteins—Prospects and Challenges," Chapter 8 of Sezer, ed., Smart Drug Delivery System, available at http://www.intechopen.com/books/smart-drug-delivery-system, Feb. 10, 2016.
Gutierrez et al., International Search Report and Written Opinion for PCT/US2015/051697, 5 pages, dated Nov. 13, 2017.
Gutierrez et al., U.S. Appl. No. 15/906,481 continuation-in-part application of U.S. Appl. No. 15/705,333, filed Feb. 27, 2018, 63 pages.
Kavecansky et al., "Advances in the delivery of RNA therapeutics: from concept to clinical reality," Genome Medicine 2017; 9:60, 16 pages.
Kavikansky & Pavlick, "Beyond Checkpoint Inhibitors: The Next Generation of Immunotherapy in Oncology," Amer. J. Hematol. Oncol. 13, 9-20, 2017.
Kontermann, "Half-life extended biotherapeutics," Expert Opin. Biol. Ther. 16, 903-15, 2016, Abstract only.
Li et al., "Discovery of peptide inhibitors targeting human programmed death 1 (PD-1) receptor," Oncotarget 7, 64967-76, Aug. 12, 2016.

(Continued)

*Primary Examiner* — Alana Harris Dent
(74) *Attorney, Agent, or Firm* — Banner & Witcoff, Ltd.

(57) ABSTRACT

This disclosure provides peptides which have a strong affinity for the checkpoint receptor "programmed death 1" (PD-1). These peptides block the interaction of PD-1 with its ligand PD-L1 and can therefore be used for various therapeutic purposes, such as inhibiting the progression of a hyperproliferative disorder, including cancer, treating infectious diseases, enhancing a response to vaccination, and treating sepsis.

19 Claims, 31 Drawing Sheets
Specification includes a Sequence Listing.

(56) References Cited

OTHER PUBLICATIONS

Magiera-Mularz et al., "Bioactive macrocyclic inhibitors of the PD-1/PD-L1 immune checkpoint," Angewandte Chemie Int. Ed. 10.1002/anie.201707707, e-published Sep. 26, 2017.

Maute et al., "Engineering high-affinity PD-1 variants for optimized immunotherapy and immuno-PET imaging," Proc. Natl. Acad. Sci. USA, E6506-E6514, published online Nov. 10, 2015.

Morrissey et al., "Immunotherapy and Novel Combinations in Oncology: Current Landscape, Challenges, and Opportunities," Clinical and Translational Science 9, 89-104, 2016.

Patel et al., "Recent Advances in Protein and Peptide Drug Delivery: A Special Emphasis on Polymeric Nanoparticles," Protein. Pept. Lett. 21, 1102-20, 2014.

Penchala et al., "A biomimetic approach for enhancing the in vivo half-life of peptides," Nat. Chem. Biol. 11, 793-98, 2015.

Rivera et al., "Hair Repigmentation During Immunotherapy Treatment With an Anti-Programmed Cell Death 1 and Anti-Programmed Cell Death Ligand 1 Agent for Lung Cancer," JAMA Dermatol. Jul. 12, 2017. doi: 10.1001/amadermatol.2017.2106, Jul. 12, 2017, Abstract only.

Sharma & Allison, "Immune Checkpoint Targeting in Cancer Therapy: Toward Combination Strategies with Curative Potential," Cell 161, 205-14, 2015.

Shindo et al., "Combination Immunotherapy with 4-1BB Activation and PD-1 Blockade Enhances Antitumor Efficacy in a Mouse Model of Subcutaneous Tumor," Anticancer Res. 35, 129-36, 2015.

Skalniak et al., "Small-molecule inhibitors of PD-1/PD-L1 immune checkpoint alleviate the PD-L1-induced exhaustion of T-cells," Oncotarget, Advance Publications, Aug. 7, 2017, 15 pages.

Smith, "Pigmented skin lesions lightened during melanoma immunotherapy," http://www.mdedge.com/edermatologynews/article/132598/melanoma/pigmented-skin-lesions-lightened-during-melanoma, Mar. 2, 2017.

Tzeng et al., "PD-1 blockage reverses immune dysfunction and hepatitis B viral persistence in a mouse animal model," PLoS One 7(6):e39179, 2012.

Van Dessel et al., "Potent and tumor specific: arming bacteria with therapeutic proteins," Ther. Deliv. 6, 385-99, 2015.

Yang et al., "Oral vaccination with *Salmonella* simultaneously expressing Yersinia pestis F1 and V antigens protects against bubonic and pneumonic plague," J Immunol. 178, 1059-67, 2007.
Ye et al., "T-cell exhaustion in chronic hepatitis B infection: current knowledge and clinical significance," Cell Death Dis. Mar 19;6:e1694, 2015.
Young et al., "Co-inhibition of CD73 and A2AR Adenosine Signaling Improves Anti-tumor Immune Responses," Cancer Cell 30, 391-403, 2016.
Zarganes-Tzitzikas et al., "Inhibitors of programmed cell death 1 (PD-1): a patent review," Expert Opinion on Therapeutic Patents 26, 973-77, published on-line Jul. 6, 2016.
Zhan et al., "From monoclonal antibodies to small molecules: the development of inhibitors targeting the PD-1/PD-L1 pathway," Drug Discovery Today 21, 1027-36, Jun. 2016.
Chang et al., "Stocking of the PD-1/PD-L1 Interaction by a D-Peptide Antagonist for Cancer Immunotherapy," Angew. Chem. Int. Ed. 54, 11769-64, 2015.

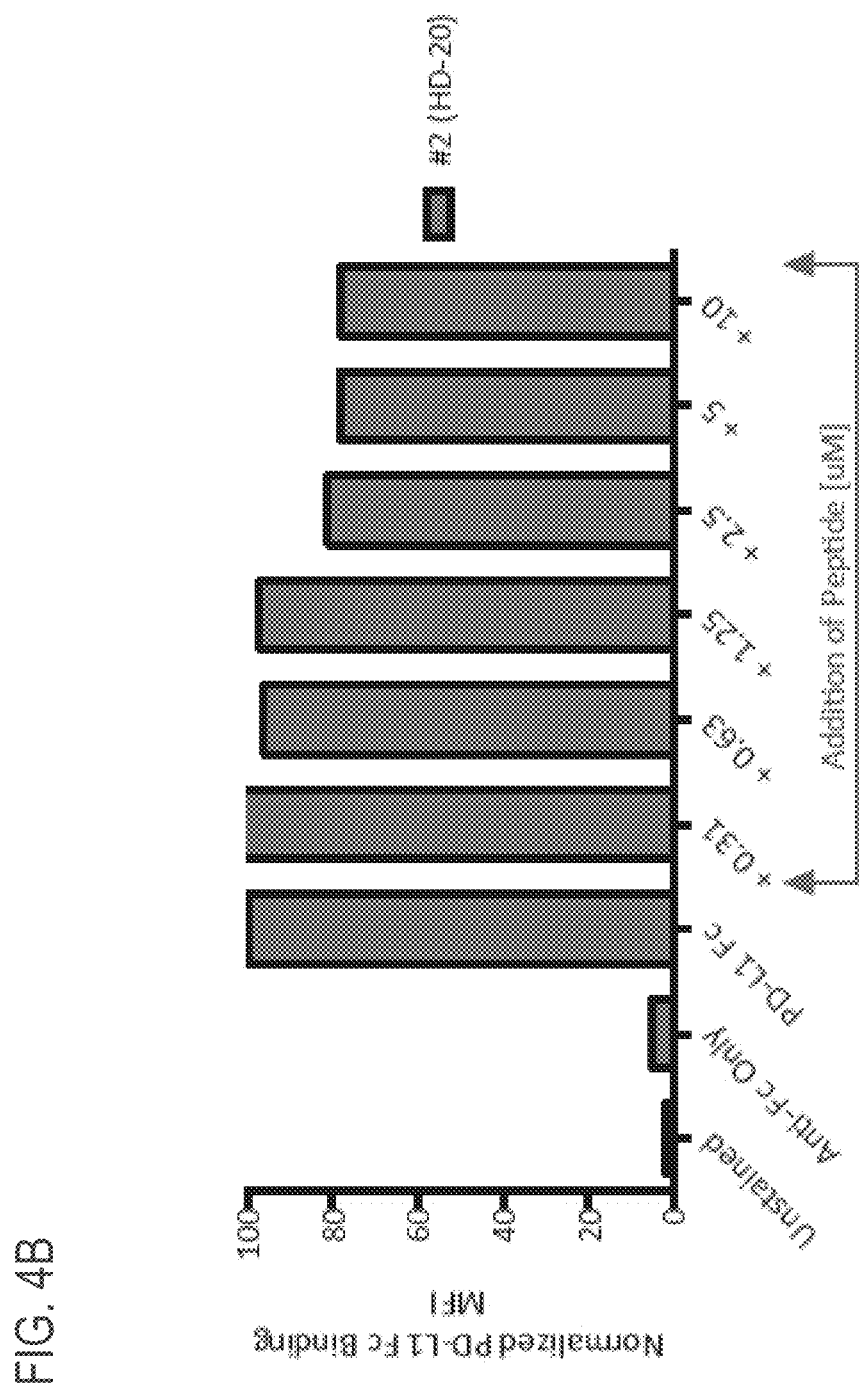

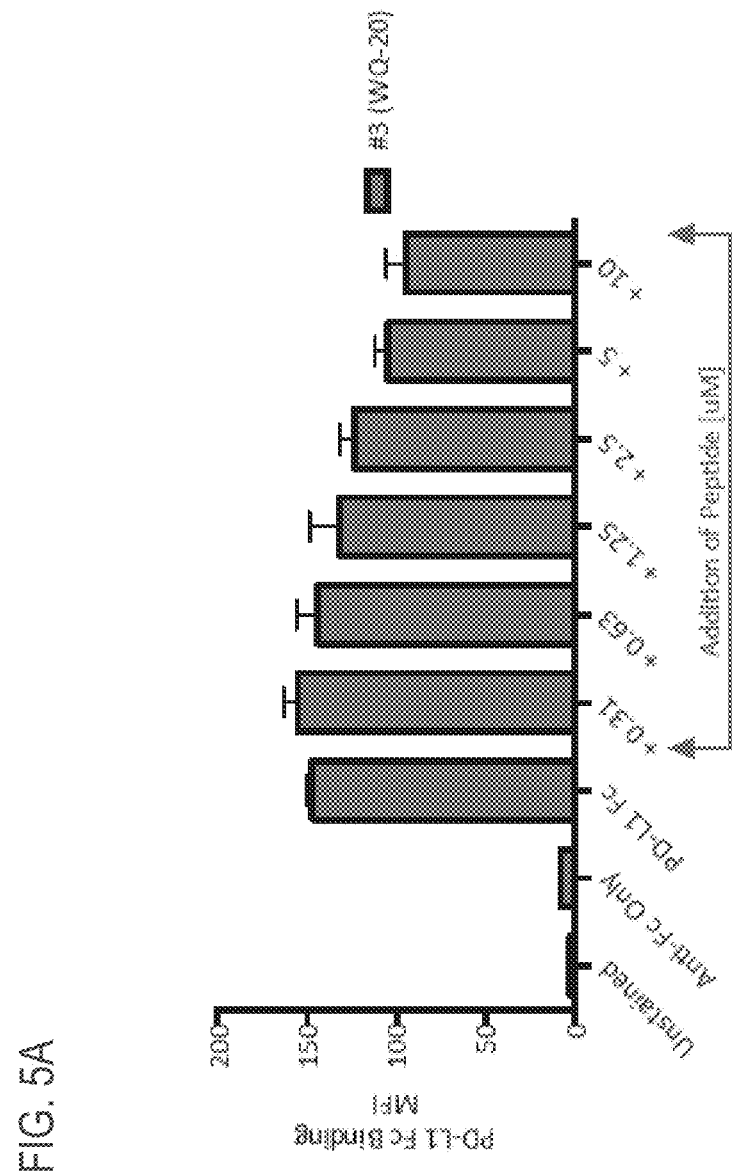

Peptide (μM)

Peptide (μM)

SEQUENCE LISTING

```
<160> NUMBER OF SEQ ID NOS: 5

<210> SEQ ID NO 1
<211> LENGTH: 20
<212> TYPE: PRT
<213> ORGANISM: Artificial Sequence
<220> FEATURE:
<223> OTHER INFORMATION: artificial peptide

<400> SEQUENCE: 1

Gln Thr Arg Thr Val Pro Met Pro Lys Ile His His Pro Pro Trp Gln
1               5                   10                  15

Asn Val Val Pro
            20

<210> SEQ ID NO 2
<211> LENGTH: 20
<212> TYPE: PRT
<213> ORGANISM: Artificial Sequence
<220> FEATURE:
<223> OTHER INFORMATION: artificial peptide

<400> SEQUENCE: 2

His His His Gln Val Tyr Gln Val Arg Ser His Trp Thr Gly Met His
1               5                   10                  15

Ser Gly His Asp
            20

<210> SEQ ID NO 3
```

```
<211> LENGTH: 21
<212> TYPE: PRT
<213> ORGANISM: Artificial Sequence
<220> FEATURE:
<223> OTHER INFORMATION: artificial peptide

<400> SEQUENCE: 3

Trp Asn Leu Pro Ala Ser Phe His Asn His His Ile Arg Pro His Glu
1               5                   10                  15

His Glu Trp Ile Gln
            20

<210> SEQ ID NO 4
<211> LENGTH: 20
<212> TYPE: PRT
<213> ORGANISM: Artificial Sequence
<220> FEATURE:
<223> OTHER INFORMATION: artificial peptide

<400> SEQUENCE: 4

Ser Ser Tyr His His Phe Lys Met Pro Glu Leu His Phe Gly Lys Asn
1               5                   10                  15

Thr Phe His Gln
            20

<210> SEQ ID NO 5
<211> LENGTH: 9
<212> TYPE: PRT
<213> ORGANISM: Plasmodium yoelii

<400> SEQUENCE: 5

Ser Tyr Val Pro Ser Ala Glu Gln Ile
1               5
```

PD-1 PEPTIDE INHIBITORS

This application claims priority to and incorporates by reference in its entirety U.S. Ser. No. 62/395,195 filed on Sep. 15, 2016. Each reference cited in this disclosure is incorporated herein in its entirety.

This application incorporates by reference the contents of a 1.38 kb text file created on Sep. 11, 2017 and named "00047900249sequencelisting.txt," which is the sequence listing for this application.

TECHNICAL FIELD

This disclosure relates generally to immunomodulatory peptides.

BRIEF DESCRIPTION OF THE DRAWINGS

FIG. 3A, MFI; FIG. 3B, normalized mean fluorescence intensity (MFI).

FIGS. 4A-B. Graphs showing effect of peptide HD20 on binding of PD-L1 to PD-1. FIG. 4A, MFI; FIG. 4B, normalized MFI.

FIGS. 5A-B. Graphs showing effect of peptide WQ20 on binding of PD-L1 to PD-1. FIG. 5A, MFI; FIG. 5B, normalized MFI.

FIG. 6A, MFI; FIG. 6B, normalized MFI.

DETAILED DESCRIPTION

Figure 1:
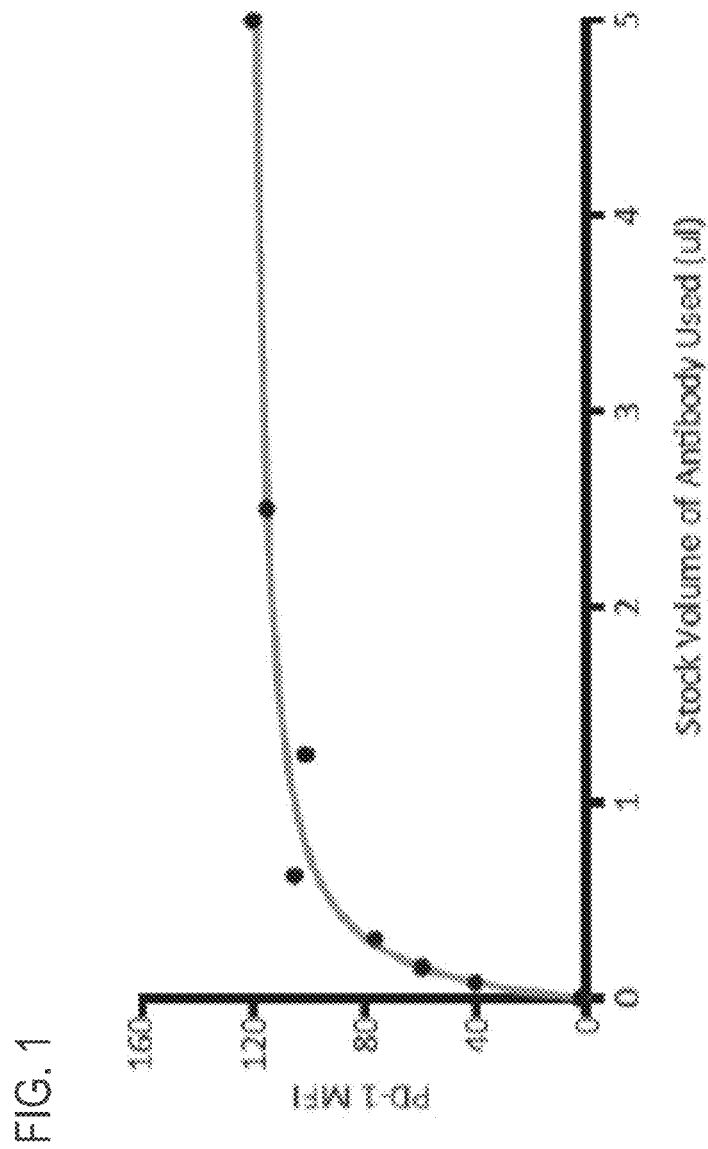
FIG. 1. Graph showing saturatable binding of anti-human PD-1 antibody to Jurkat cells.

This disclosure provides four peptides:

| peptide | amino acid sequence | SEQ ID NO: |
|---|---|---|
| QP20 | QTRTVPMPKIHHPPWQNVVP | 1 |
| HD20 | HHHQVYQVRSHWTGMHSGHD | 2 |
| WQ20 | WNLPASFHNHHIRPHEHEWIQ | 3 |
| SQ20 | SSYHHFKMPELHFGKNTFHQ | 4 |

These peptides share a core sequence of HH_, which is shown above in bold, and have a strong affinity for the checkpoint receptor "programmed death 1" (PD-1). These peptides block the interaction of PD-1 with its ligand PD-L1 and can therefore be used to inhibit the progression of a hyperproliferative disorder, including cancer, or to treat infectious diseases, including persistent infections by agents such as HIV, hepatitis B virus (HBV), hepatitis C virus (HCV), and *Plasmodium falciparum*, by enhancing, stimulating, and/or increasing an individual's immune response.

Pharmaceutical Compositions

Pharmaceutical compositions comprise up to four of the peptides disclosed herein and a pharmaceutically acceptable vehicle. The "pharmaceutically acceptable vehicle" may comprise one or more substances which do not affect the biological activity of the peptides and, when administered to a patient, does not cause an adverse reaction. Pharmaceutical compositions may be liquid or may be lyophilized. Lyophilized compositions may be provided in a kit with a suitable liquid, typically water for injection (WFI) for use in reconstituting the composition. Pharmaceutical compositions can be administered by any suitable route, including, but not limited to, intravenous, intramuscular, intradermal, intraperitoneal, and subcutaneous administration.

In some embodiments, one or more of the disclosed peptides can be conjugated to various moieties, such as albumin and transthyretin, to enhance the peptide's plasma half-life. Methods of preparing such conjugates are well known in the art (e.g., Penchala et al., 2015; Kontermann, 2016; Zorzi et al., 2017).

Therapeutic Uses

Pharmaceutical compositions disclosed herein have a number of therapeutic applications. In some embodiments, a pharmaceutical composition disclosed herein can be administered to a patient to inhibit the progression of a hyperproliferative disorder, such as cancer. Such inhibition may include, for example, reducing proliferation of neoplastic or pre-neoplastic cells; destroying neoplastic or pre-neoplastic cells; and inhibiting metastasis or decreasing the size of a tumor.

Examples of cancers that can be treated using a pharmaceutical composition disclosed herein include, but are not limited to, melanomas, lymphomas, sarcomas, and cancers of the colon, kidney, stomach, bladder, brain (e.g., gliomas, glioblastomas, astrocytomas, medulloblastomas), prostate, bladder, rectum, esophagus, pancreas, liver, lung, breast, uterus, cervix, ovary, blood (e.g., acute myeloid leukemia, acute lymphoid leukemia, chronic myeloid leukemia, chronic lymphocytic leukemia, Burkitt's lymphoma, EBV-induced B-cell lymphoma).

In some embodiments, a pharmaceutical composition disclosed herein can be administered in conjunction with a cancer vaccine. A "cancer vaccine" is an immunogenic composition intended to elicit an immune response against a particular antigen in patient to which the cancer vaccine is administered. A cancer vaccine typically contains a tumor antigen which is able to induce or stimulate an immune response against the tumor antigen. A "tumor antigen" is an antigen that is present on the surface of a target tumor. A tumor antigen may be a molecule which is not expressed by a non-tumor cell or may be, for example, an altered version of a molecule expressed by a non-tumor cell (e.g., a protein that is misfolded, truncated, or otherwise mutated). "In conjunction with" includes administration of the pharmaceutical composition may be together with, before, or after administration of the cancer vaccine.

In some embodiments, a pharmaceutical composition disclosed herein can be administered in conjunction with a chimeric antigen receptor (CAR) T cell therapy to treat cancers in order to increase the efficacy of such therapy.

In some embodiments, a pharmaceutical composition disclosed herein can be administered to a patient to treat infectious diseases, including chronic infections, caused, e.g., by viruses, fungi, bacteria, and protozoa, and helminths.

Examples of viral agents include human immunodeficiency virus (HIV), Epstein Barr Virus (EBV), Herpes simplex (HSV, including HSV1 and HSV2), Human Papillomavirus (HPV), Varicella zoster (VSV) Cytomegalovirus (CMV), and hepatitis A, B, and C viruses.

Examples of fungal agents include *Aspergillus, Candida, Coccidioides, Cryptococcus*, and *Histoplasma capsulatum*.

Examples of bacterial agents include Streptococcal bacteria (e.g., *pyogenes, agalactiae, pneumoniae*), *Chlamydia pneumoniae, Listeria monocytogenes*, and *Mycobacterium tuberculosis*.

Examples of protozoa include *Sarcodina* (e.g., *Entamoeba*), *Mastigophora* (e.g., *Giardia*), *Ciliophora* (e.g., *Balantidium*), and *Sporozoa* (e.g., *Plasmodium falciparum, Cryptosporidium*).

Examples of helminths include *Platyhelminths* (e.g., trematodes, cestodes), *Acanthocephalins*, and *Nematodes*.

In some embodiments a pharmaceutical composition disclosed herein can be administered as a vaccine adjuvant in conjunction with a vaccine to enhance a response to vaccination (e.g., by increasing effector T cells and/or reducing T cell exhaustion). "In conjunction with" includes administration of the pharmaceutical composition may be together with, before, or after administration of, the vaccine. The vaccine can be, for example, an RNA vaccine (e.g., US 2016/0130345, US 2017/0182150), a DNA vaccine, a recombinant vector, a protein vaccine, or a peptide vaccine. Such vaccines can be delivered, for example, using virus-like particles, as is well known in the art.

In some embodiments a pharmaceutical composition disclosed herein can be administered to treat sepsis.

Example 1. Peptide Library Screening

The TriCo-20™ (TRICO-20™) and TriCo-16™ (TRICO-16™) Phage Display Peptide Libraries (Creative Biolabs, 45-1 Ramsey Road, Shirley, N.Y. 11967) were screened to identify binders of soluble recombinant human PD-1 receptor. After the fourth round of panning, obvious enrichment for specific binders was observed, and individual peptides were confirmed as weakly specific binders in a clonal phage ELISA. A fifth round of panning led to greater enrichment. Table 1 lists four peptides which showed strong specific binding in the clonal phage ELISA.

TABLE 1

| Clone | Clonal Phase ELISA coated signal | uncoated signal | peptide sequence | SEQ ID NO: |
|---|---|---|---|---|
| QP20 | 0.851 | 0.446 | QTRTVPMPKIHHPPWQNVVP | 1 |
| HD20 | 0.281 | 0.109 | HHHQVYQVRSHWTGMHSGHD | 2 |
| WQ20 | 0.275 | 0.115 | WNLPASFHNHHIRPHEHEWIQ | 3 |
| SQ20 | 0.284 | 0.159 | SSYHHFKMPELHFGKNTFHQ | 4 |

Example 2. Competitive PD-1:PD-L1 Binding Inhibition Assay

Briefly, detection of cell surface PD-1 on Jurkat cells was accomplished by incubating cells with the human PD-L1-Fc fusion protein, followed by detection of the recombinant molecule with a fluorescently labeled anti-human Fc antibody. Flow cytometry was performed to detect binding between PD-1 and the PD-L1 recombinant protein. Quantitative binding measurement was then determined by mean fluorescence intensity (MFI).

Figure 2:
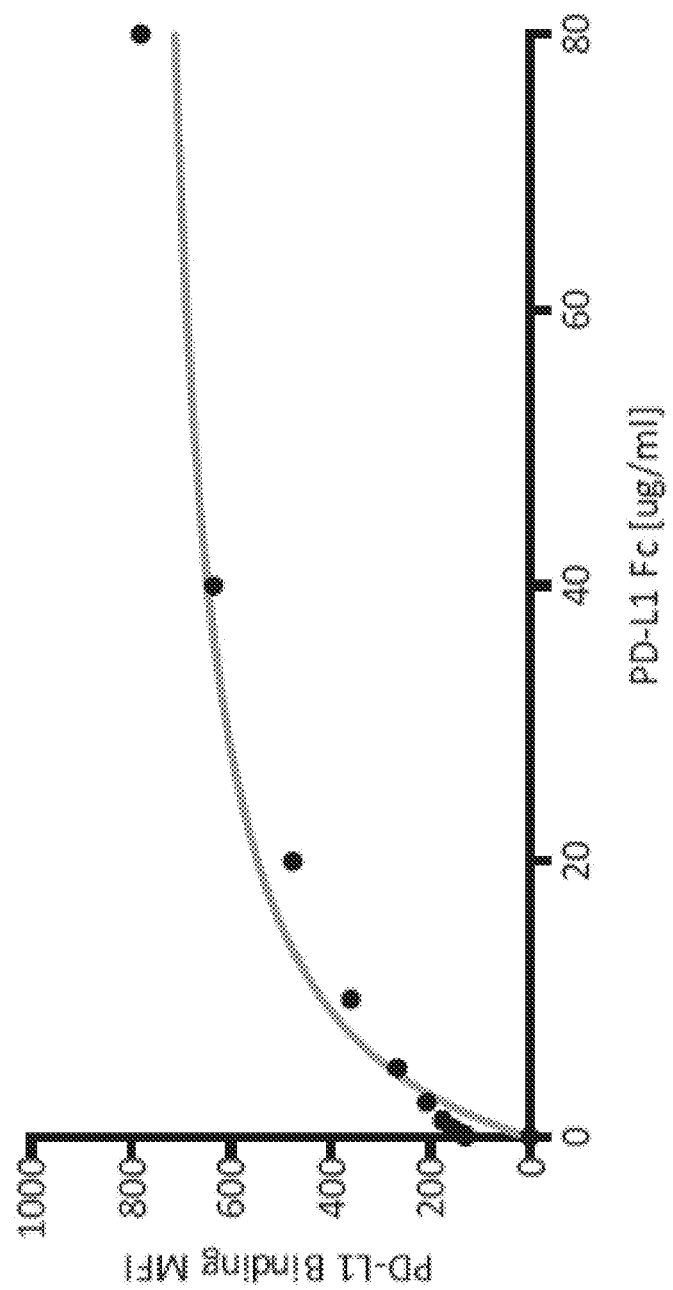
FIG. 2. Graph showing saturatable binding of PD-L1 Fc to Jurkat cells.
Figure 3A:
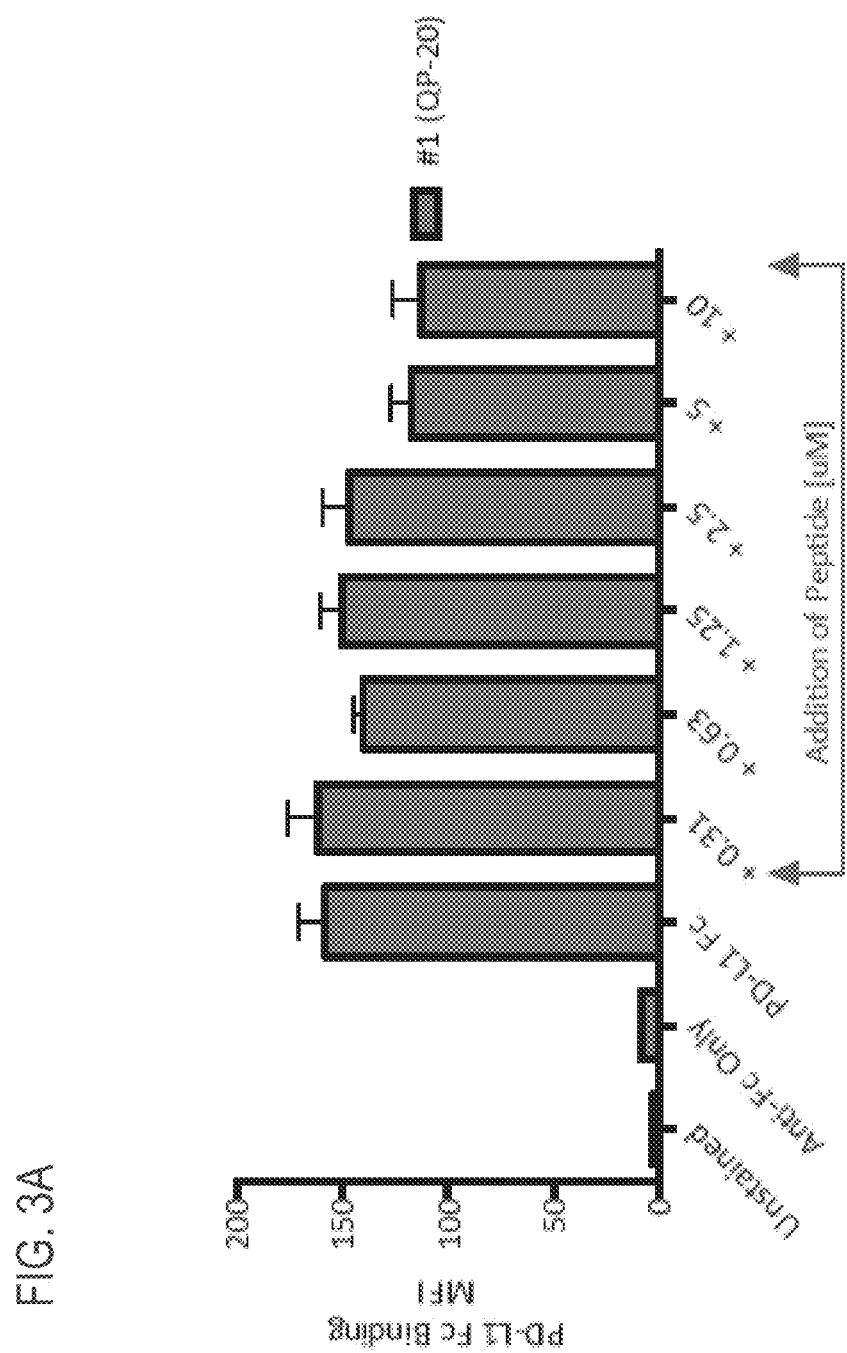
FIGS. 3A-B. Graphs showing effect of peptide QP20 on binding of PD-L1 to PD-1.
Figure 3B:
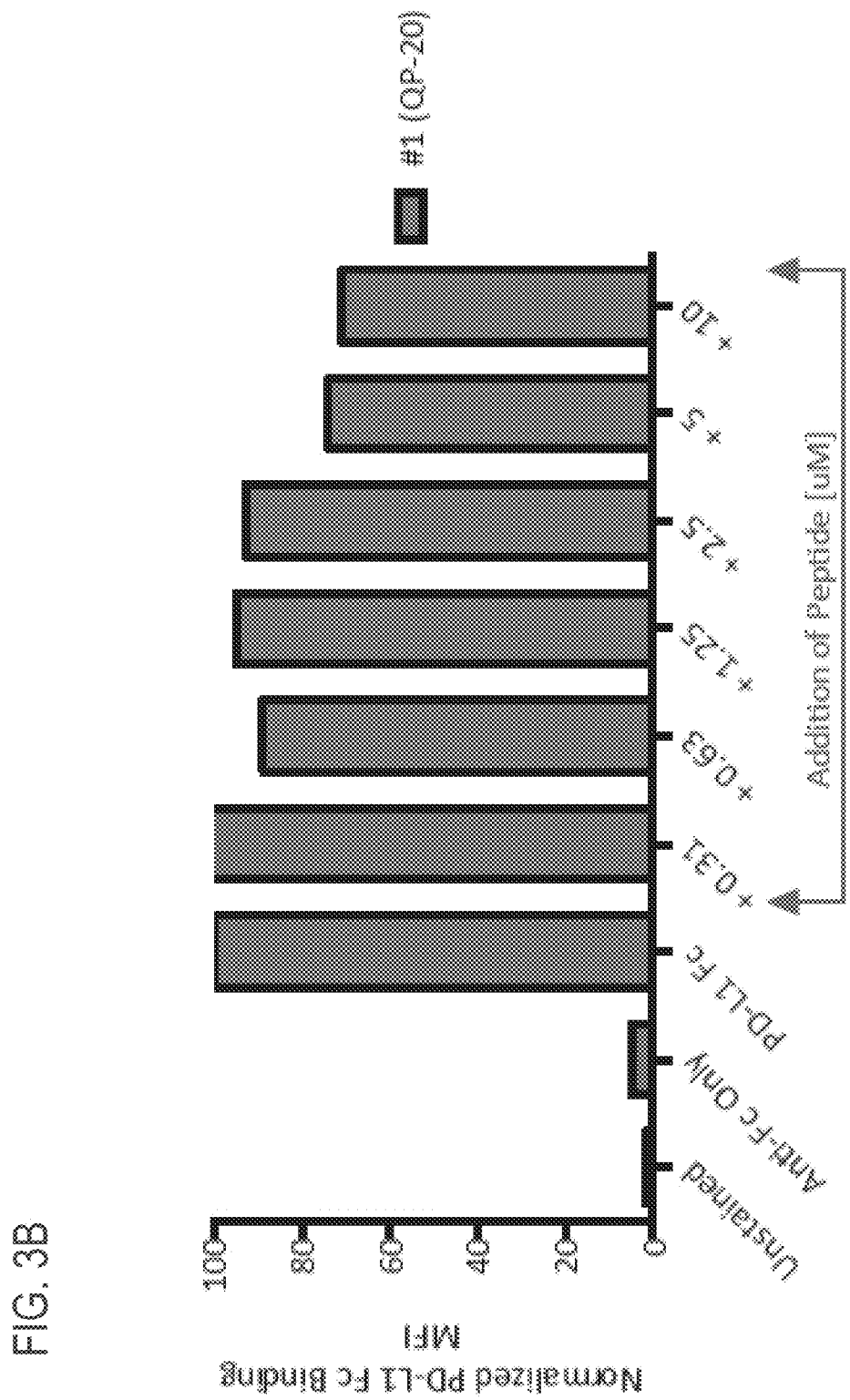
Figure 4A:
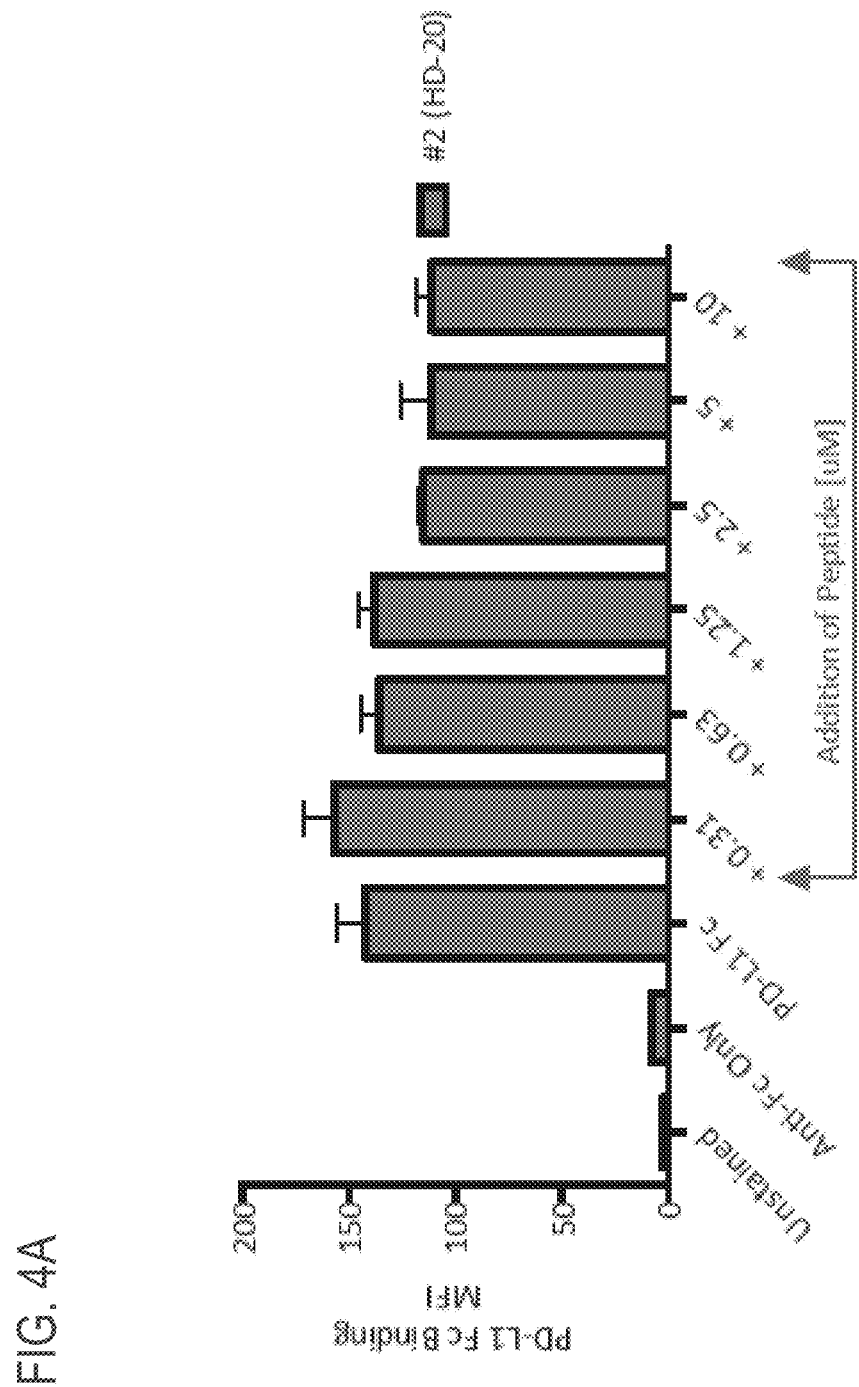
Figure 5B:
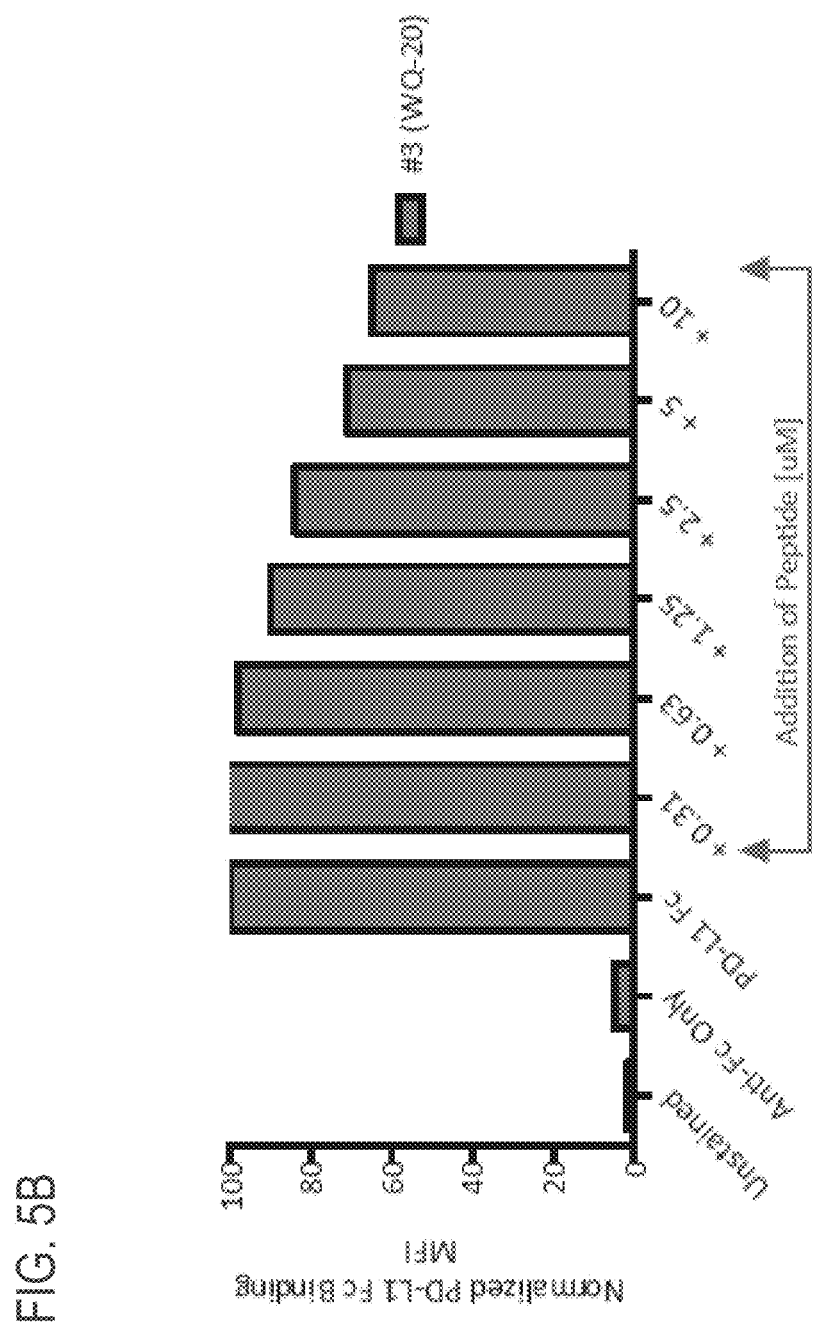
Figure 6A:
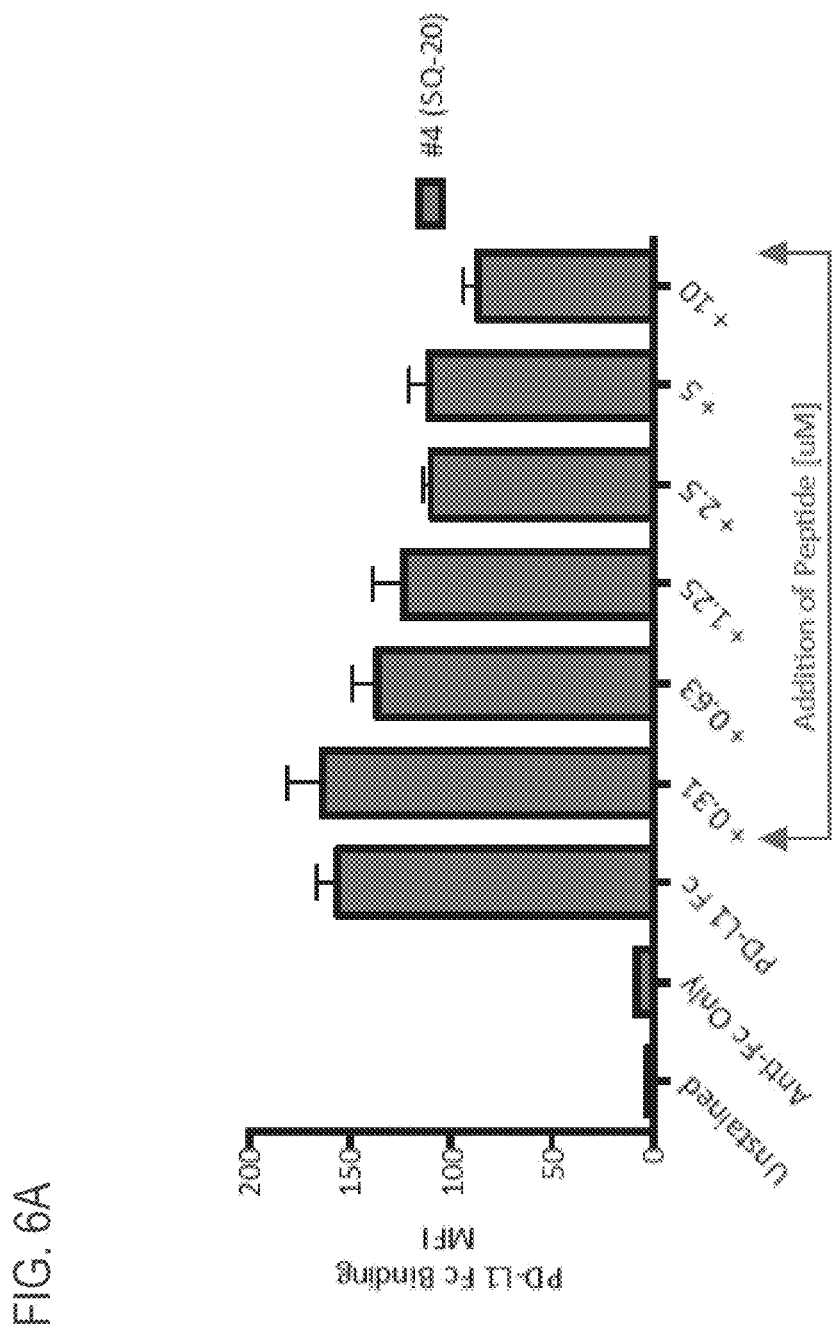
FIGS. 6A-B. Graphs showing effect of peptide SQ20 on binding of PD-L1 to PD-1.
Figure 6B:
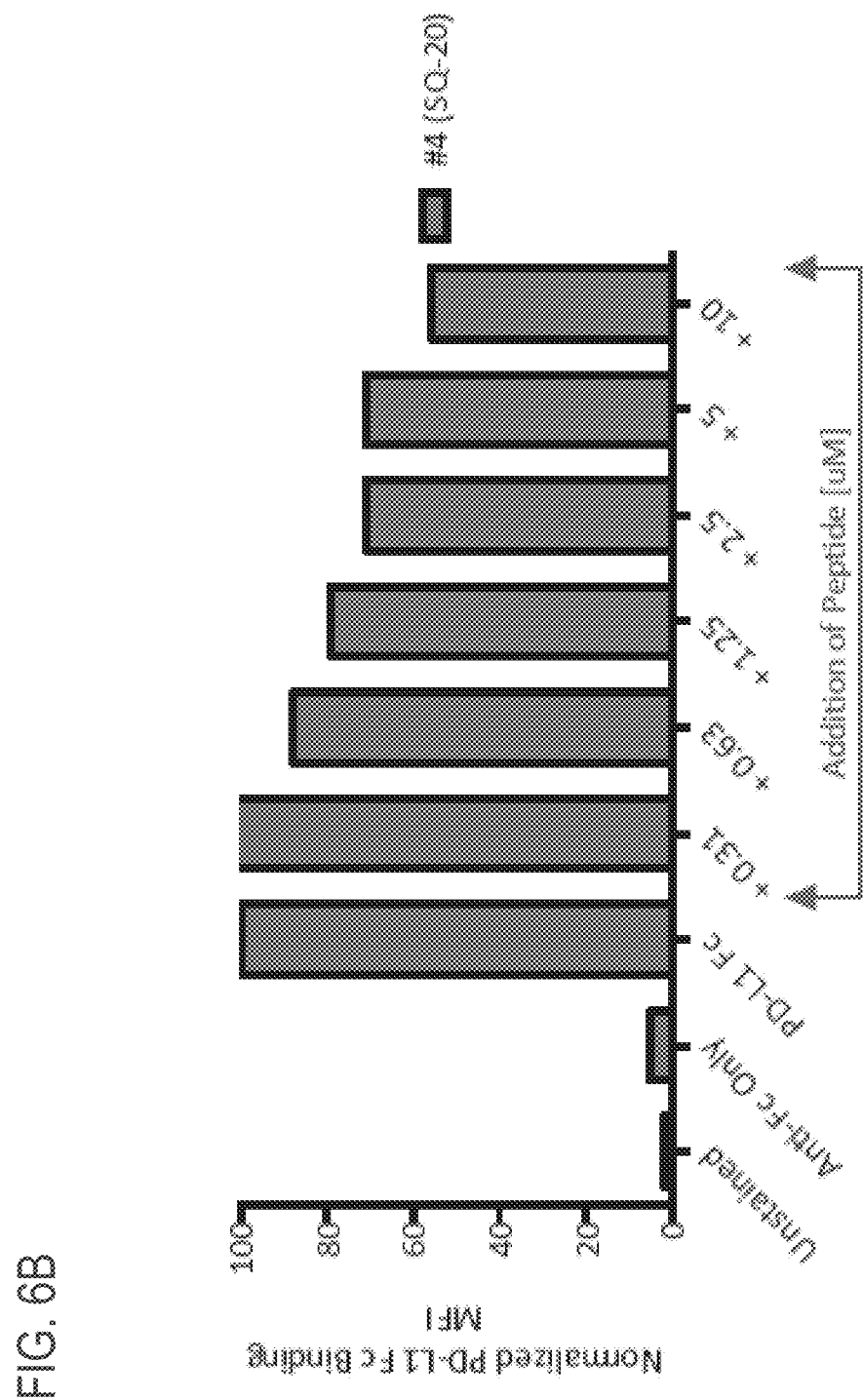

Jurkat Cell-surface expression of PD1 and binding of PD-L1 to these cells were verified as shown in FIGS. 1 and 2. The results are shown in FIGS. 3A-B, 4A-B, 5A-B, and 6A-B.

Example 3. Cell-Based Reporter Assay

A cell-based reporter assay was used to assess whether binding of the four peptides identified above was sufficient to block the interaction with PD-1 and its ligand PD-L1. The components of the assay include a Jurkat T cell line that stably expresses human PD-1 and a luciferase reporter, a CHO cell line that stably expressed human PD-L1, and a positive control anti-PD-1 antibody that blocks the interaction of PD-1 and PD-L1, resulting in a measurable effect in the assay. The luciferase reporter in the Jurkat T cell line is triggered by IL-1, NFAT, or NF-κB response elements in the promoter region. The Jurkat T cells are pre-treated with CD3 and immediately cryopreserved for use in the assay. Interaction of the Jurkat T cells with the PD-L1 expressing cell line inhibits the intracellular mechanism by which the luciferase construct is activated, thereby preventing luciferase expression. A molecule that binds to either PD-1 on the Jurkat T cells or to PD-L1 on the CHO cells sufficiently to prevent their interaction permits the Jurkat T cells to produce luciferase. CellTiter-Glo® (CELLTITER-GLO®, Promega) was used to measure luciferase expression.

Figure 7A:
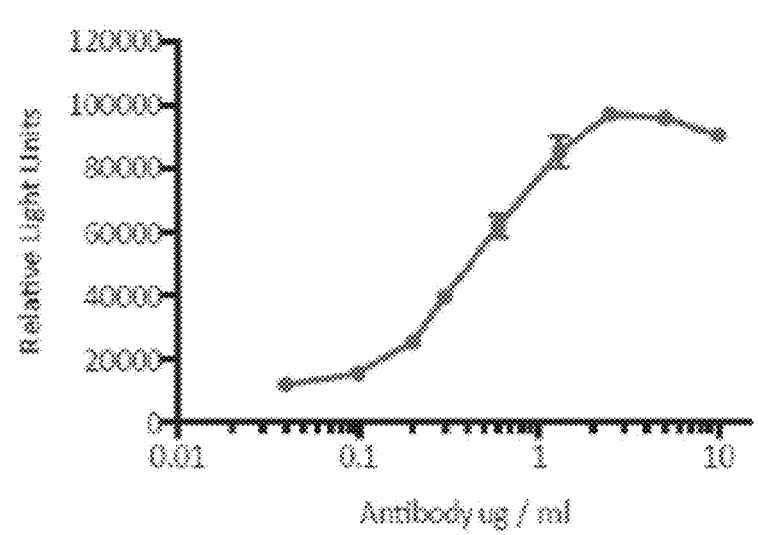
FIG. 7A. Graph showing the effect of an anti-human PD-1 antibody on the interaction between PD-1-expressing Jurkat T cells and PD-L1-expressing CHO cells that results in inhibition of a PD-1 mediated suppression of luciferase reporter that is under the control of promoter containing IL-2, NFAT, and NF-kB response elements.
Figure 7B:
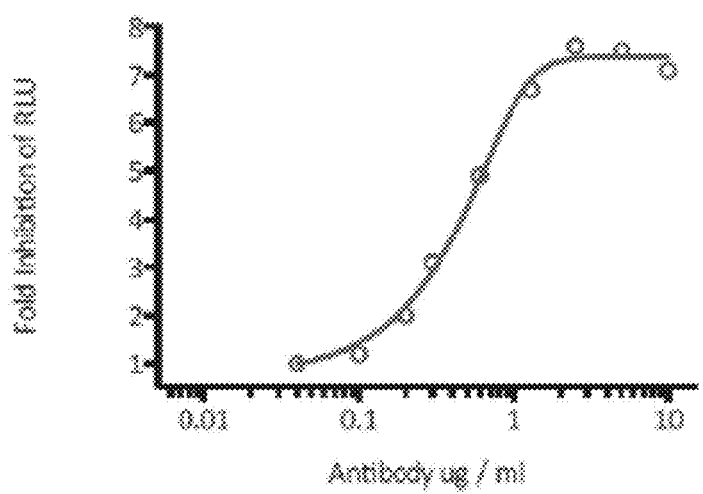
FIG. 7B. Graph showing the effect of an anti-human PD-1 antibody on the interaction between PD-1-expressing Jurkat T cells and PD-L1-expressing CHO cells (data in 7A expressed as fold inhibition).

The results of positive control assays using the anti-PD-1 control antibody are shown in FIGS. 7A-B. These results demonstrate that the control antibody restores luciferase expression in a dose-dependent manner, with peak-fold inhibition of approximately 8 at an antibody concentration of 20 μM.

Figure 8A:
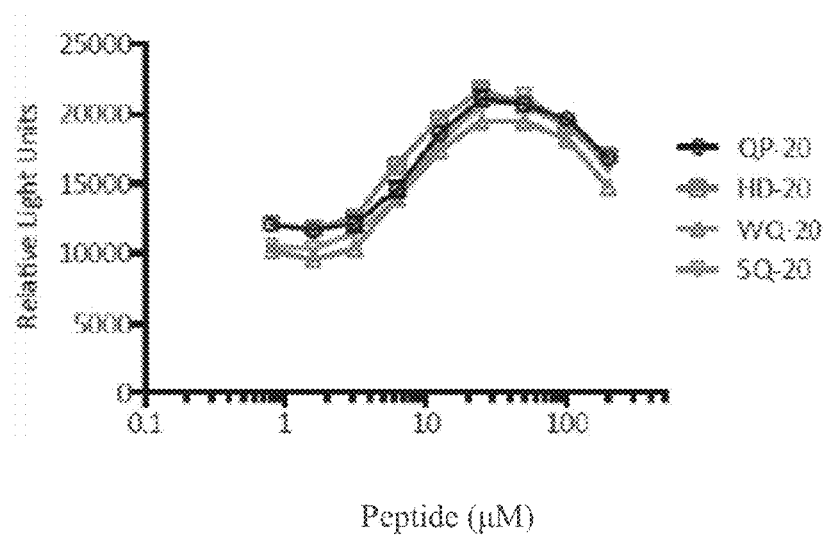
FIG. 8A. Graph showing that PD-1 peptide inhibitors inhibit, in a dose-dependent manner, the interaction between PD-1-expressing Jurkat T cells and PD-L1-expressing CHO cells, which results in increased luciferase reporter expression.
Figure 8B:
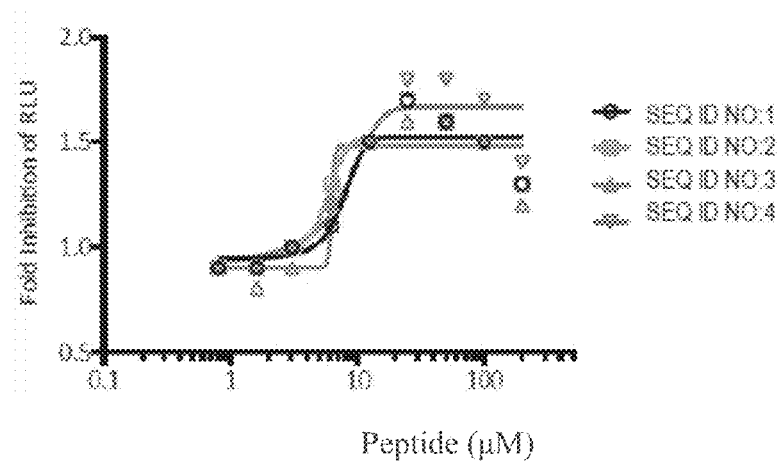
FIG. 8B. Graph showing the effect of an anti-human PD-1 antibody on the interaction between PD-1-expressing Jurkat T cells and PD-L1-expressing CHO cells (data in 8B expressed as fold inhibition).
Figure 9:
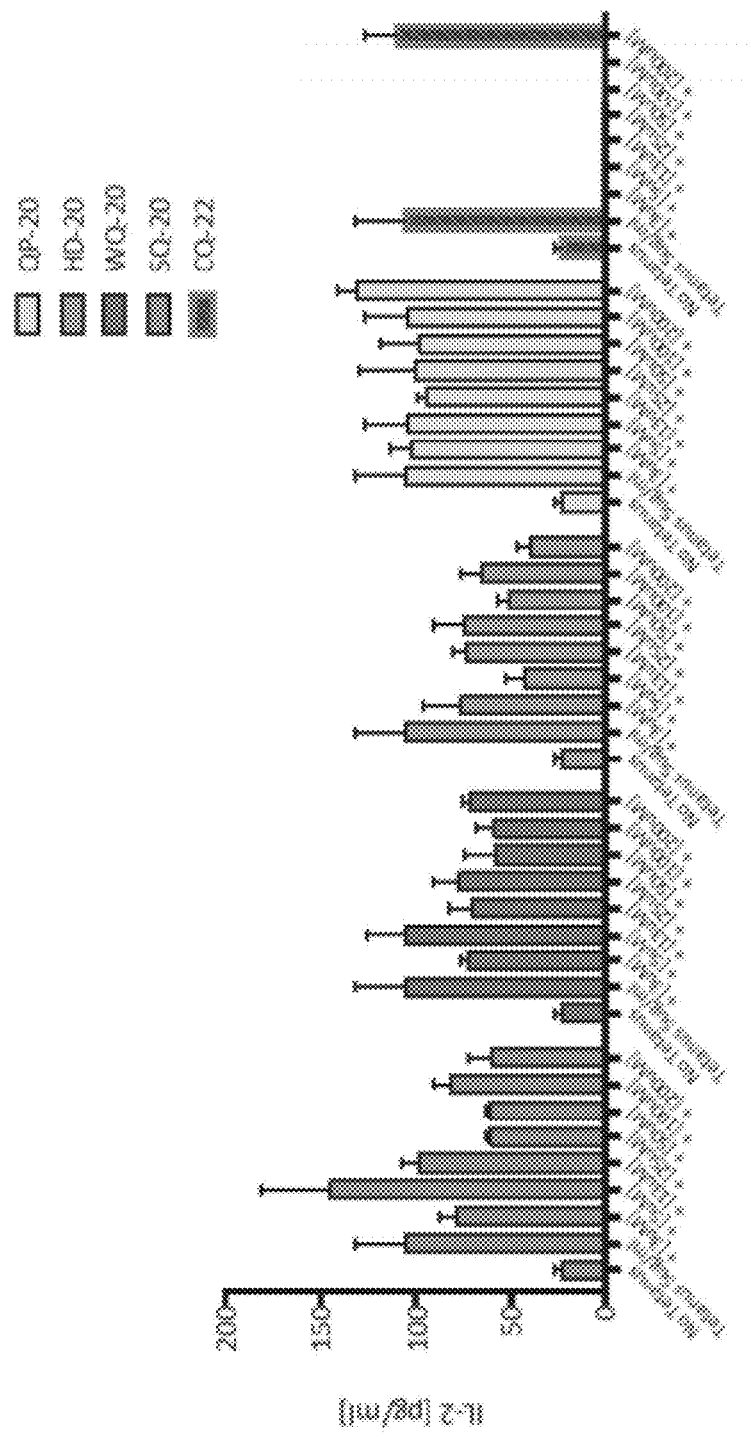
FIG. 9. Graph showing IL-2 production by peripheral blood mononuclear cells (PBMCs) in a tetanus toxoid recall assay after culture with peptides QP20, HD20, WQ20, SQ20, or CQ-22.
Figure 10:
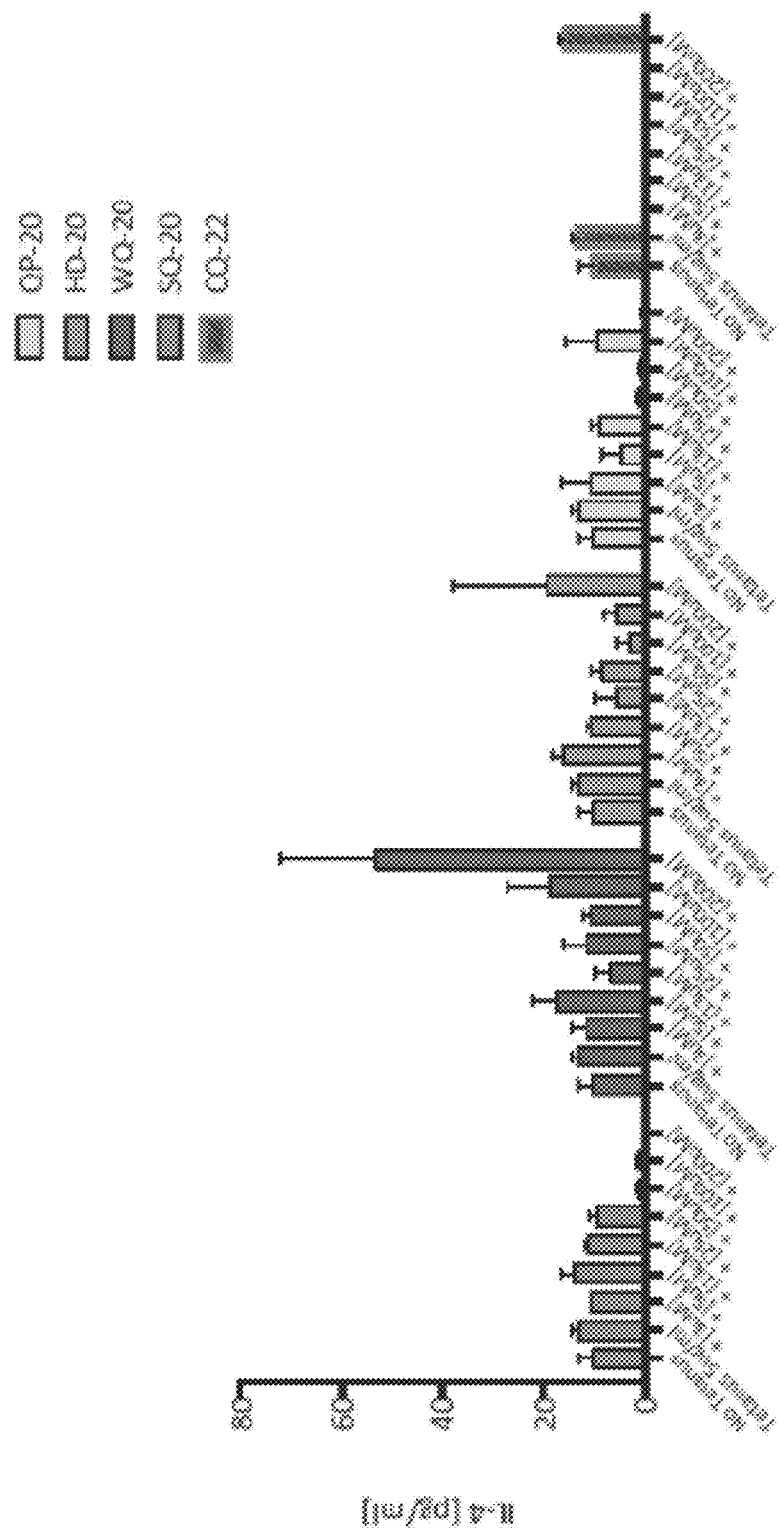
FIG. 10. Graph showing IL-4 production by PBMCs in a tetanus toxoid recall assay after culture with peptides QP20, HD20, WQ20, SQ20, or CQ-22.
Figure 11:
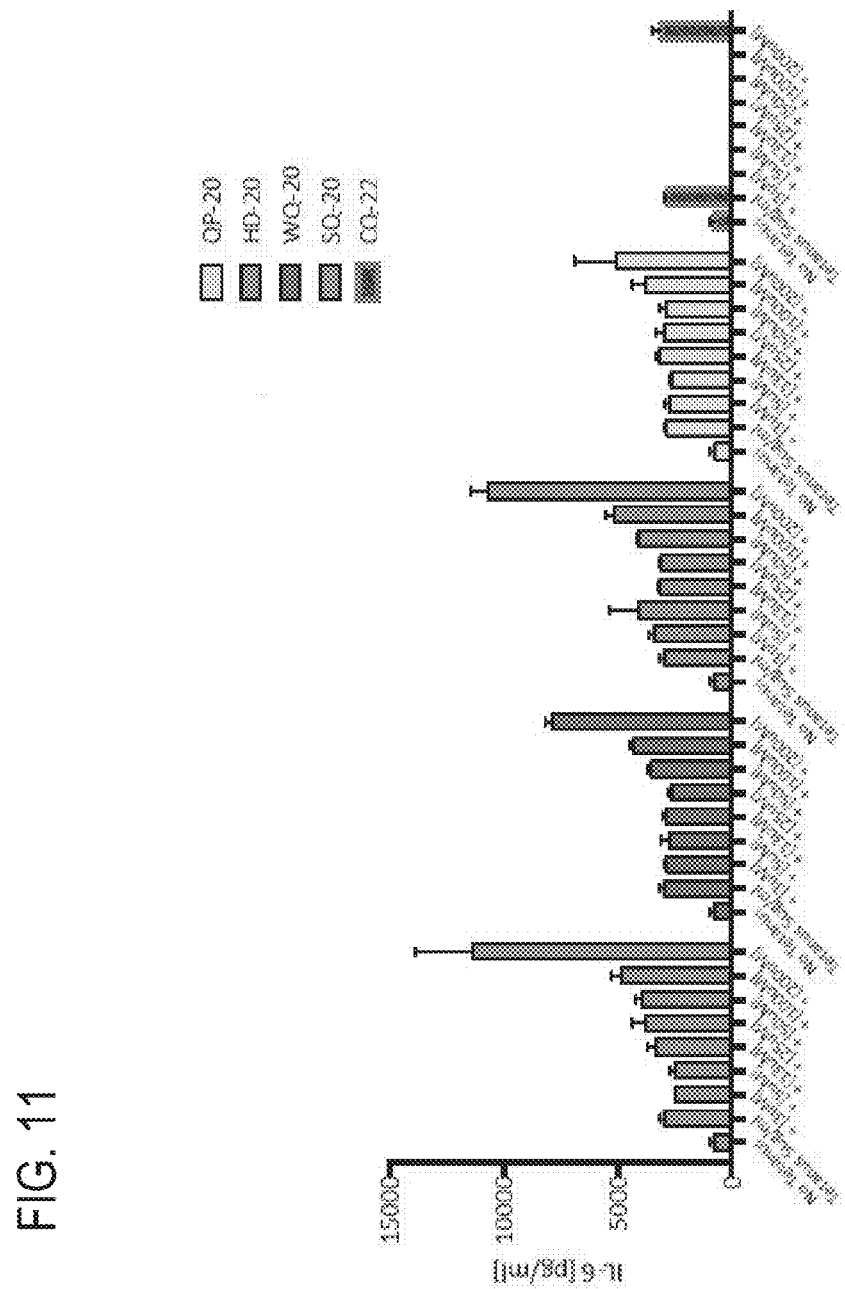
FIG. 11. Graph showing IL-6 production by PBMCs in a tetanus toxoid recall assay after culture with peptides QP20, HD20, WQ20, SQ20, or CQ-22.
Figure 12:
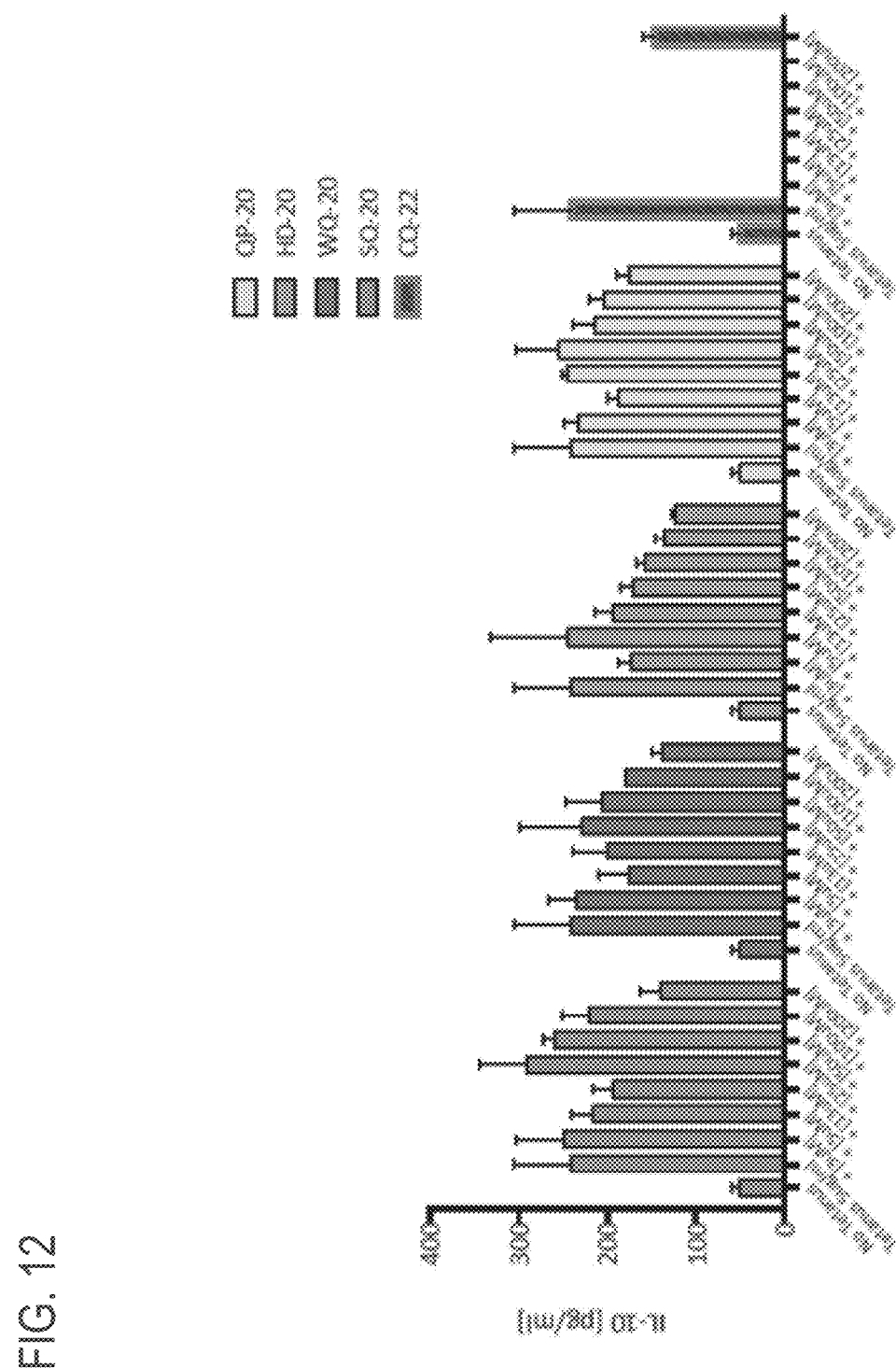
FIG. 12. Graph showing IL-10 production by PBMCs in a tetanus toxoid recall assay after culture with peptides QP20, HD20, WQ20, SQ20, or CQ-22.
Figure 13:
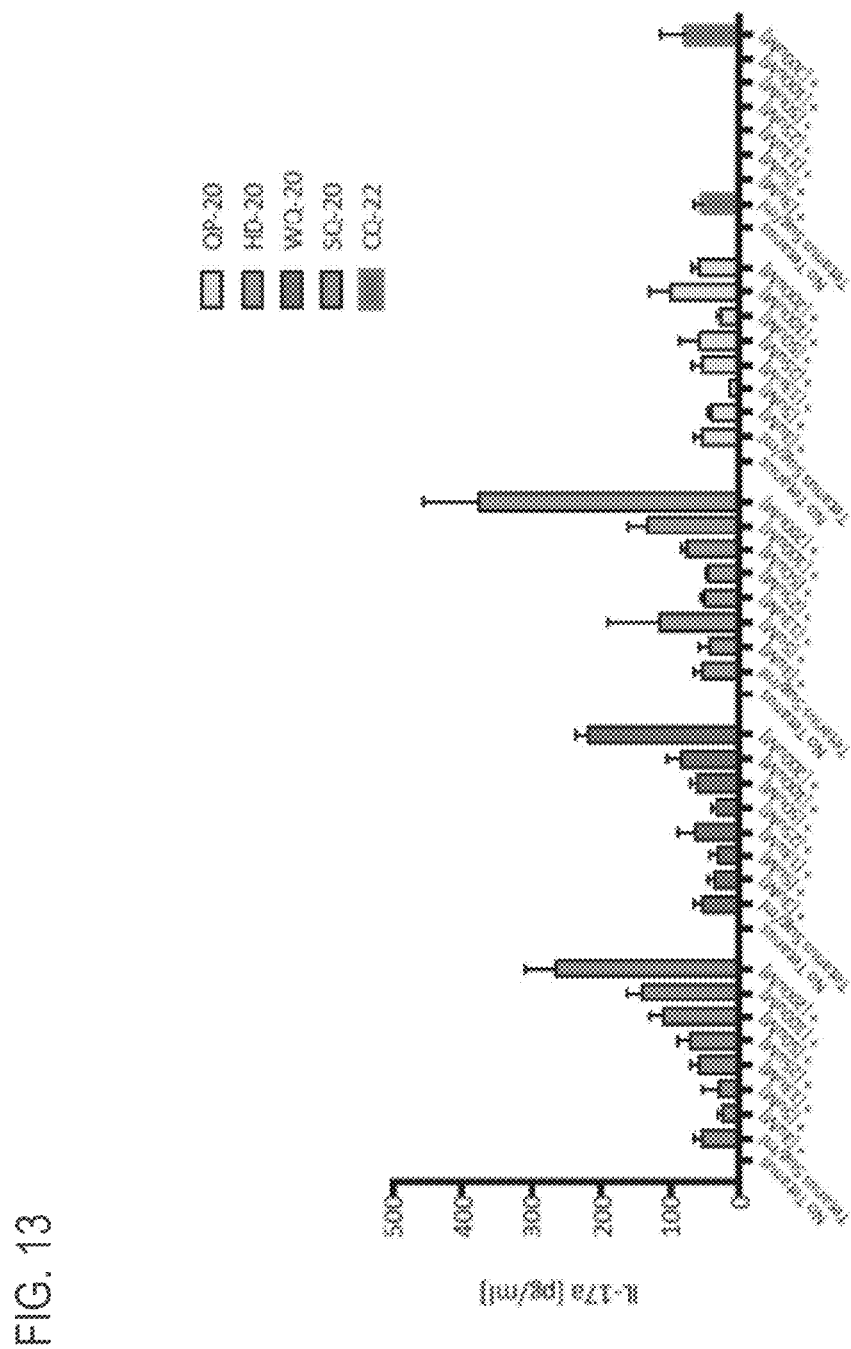
FIG. 13. Graph showing IL-17a production by PBMCs in a tetanus toxoid recall assay, after culture with peptides QP20, HD20, WQ20, SQ20, or CQ-22.
Figure 14:
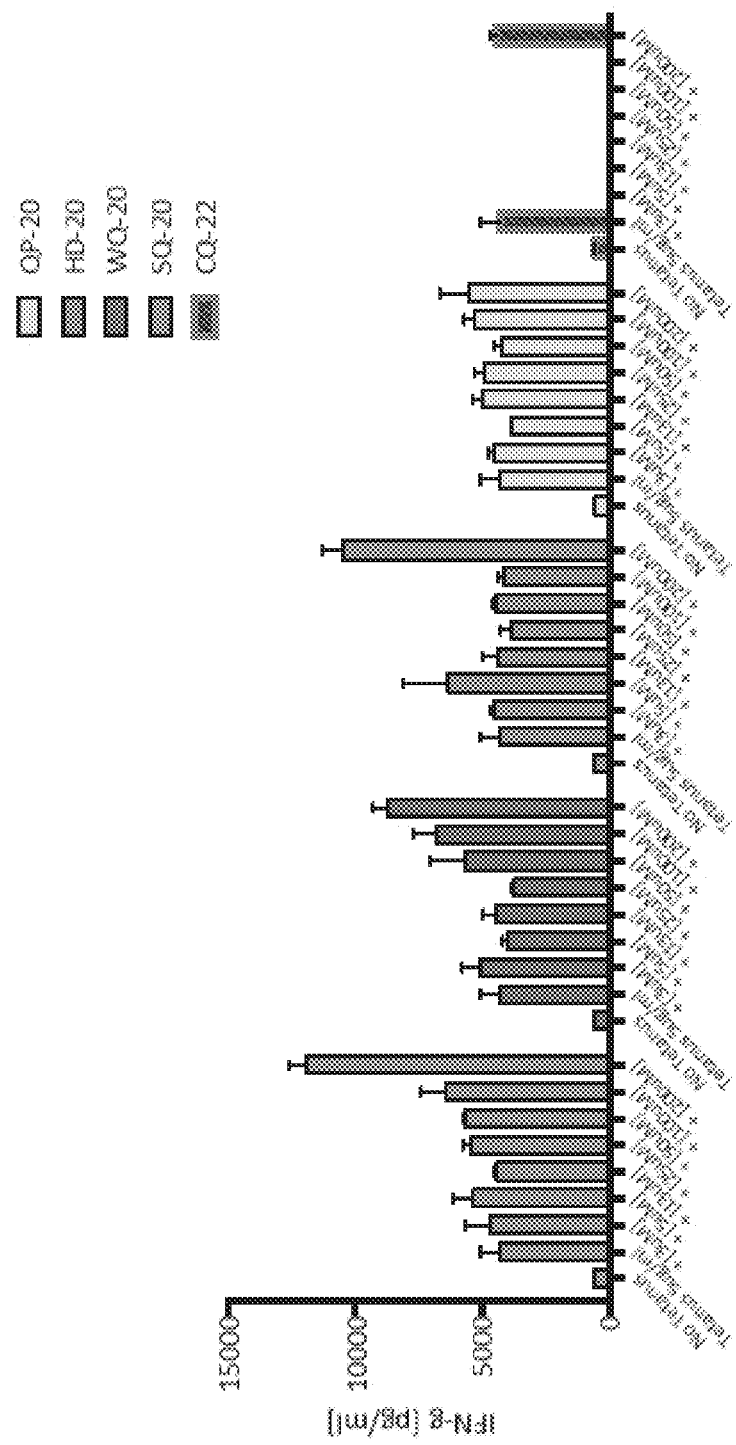
FIG. 14. Graph showing IFNγ production by PBMCs in a tetanus toxoid recall assay, after culture with peptides QP20, HD20, WQ20, SQ20, or CQ-22.
Figure 15:
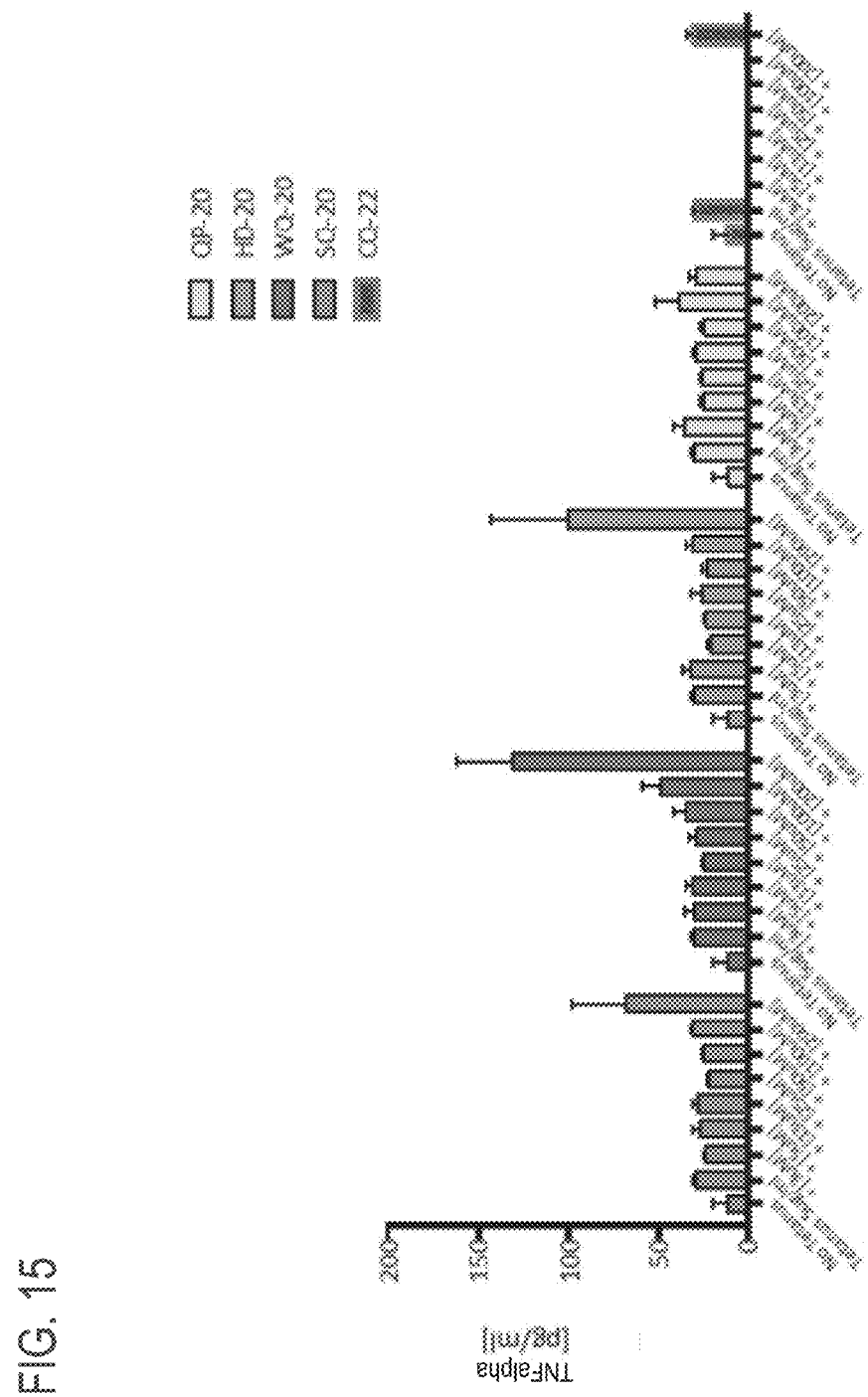
FIG. 15. Graph showing TNFα production by PBMCs in a tetanus toxoid recall assay, after culture with peptides QP20, HD20, WQ20, SQ20, or CQ-22.
Figure 16:
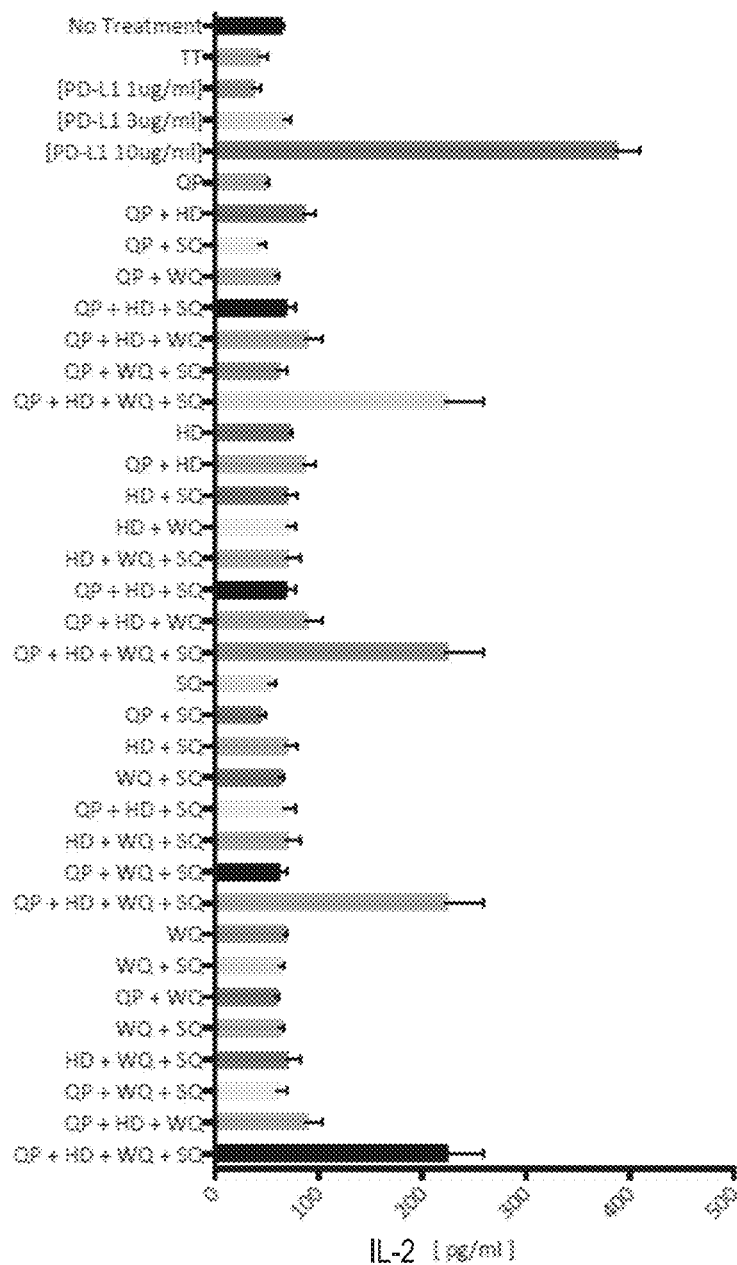
FIG. 16. Graph showing IL-2 production by PBMCs in a tetanus toxoid recall assay, after culture with various combinations of peptides QP20, HD20, WQ20, and SQ20.
Figure 17:
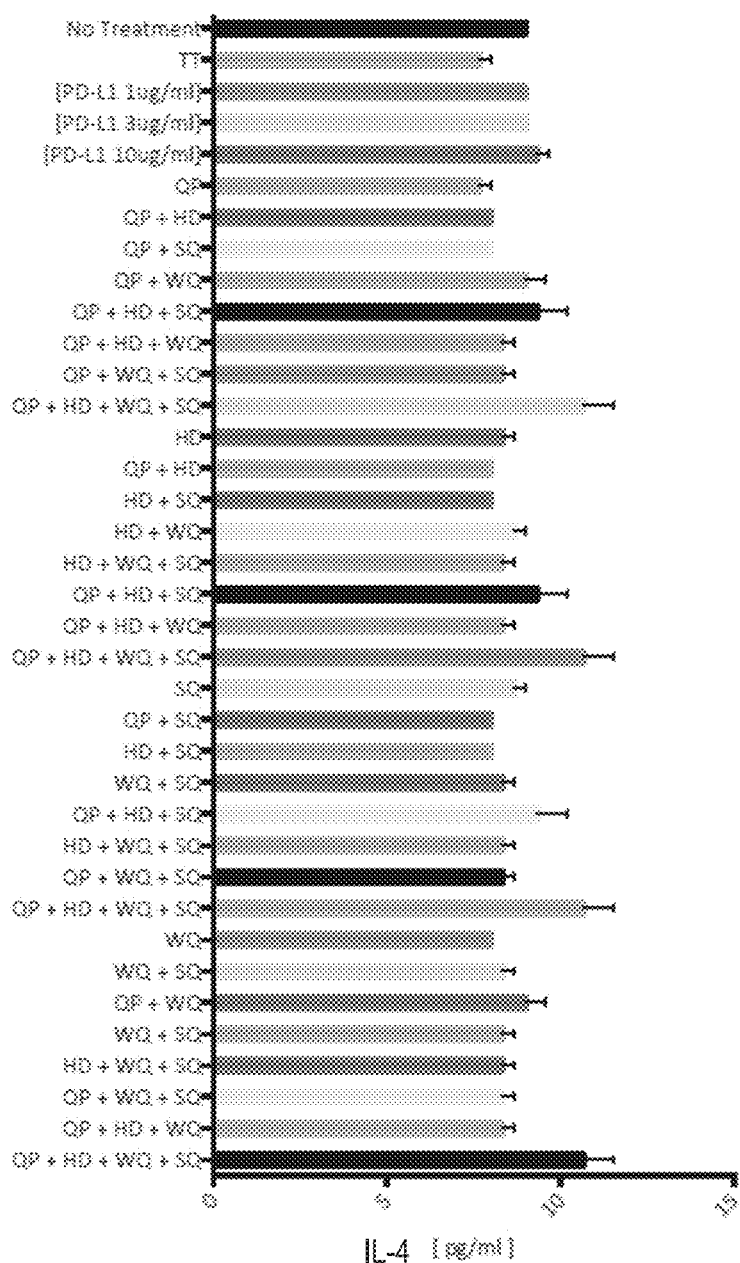
FIG. 17. Graph showing IL-4 production by PBMCs in a tetanus toxoid recall assay, after culture with various combinations of peptides QP20, HD20, WQ20, and SQ20.
Figure 18:
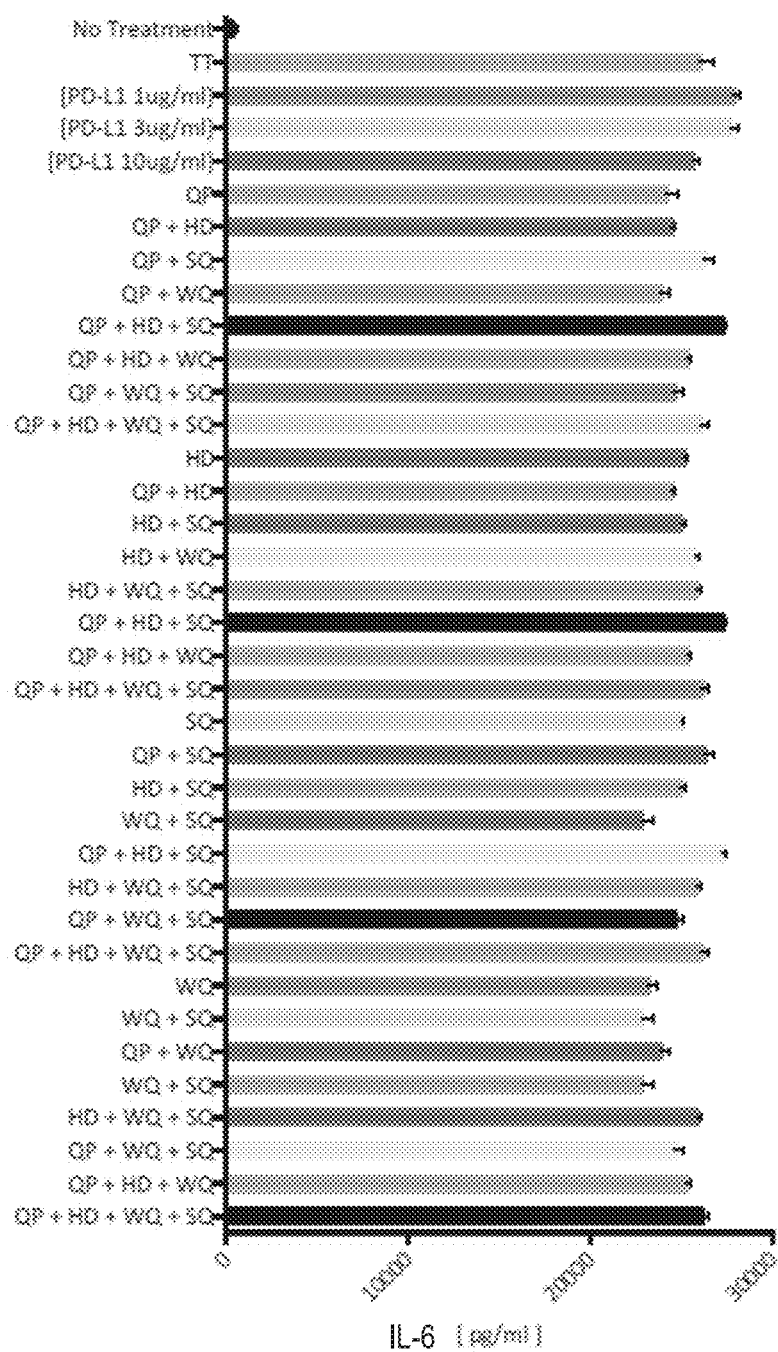
FIG. 18. Graph showing IL-6 production by PBMCs in a tetanus toxoid recall assay, after culture with various combinations of peptides QP20, HD20, WQ20, and SQ20.
Figure 19:
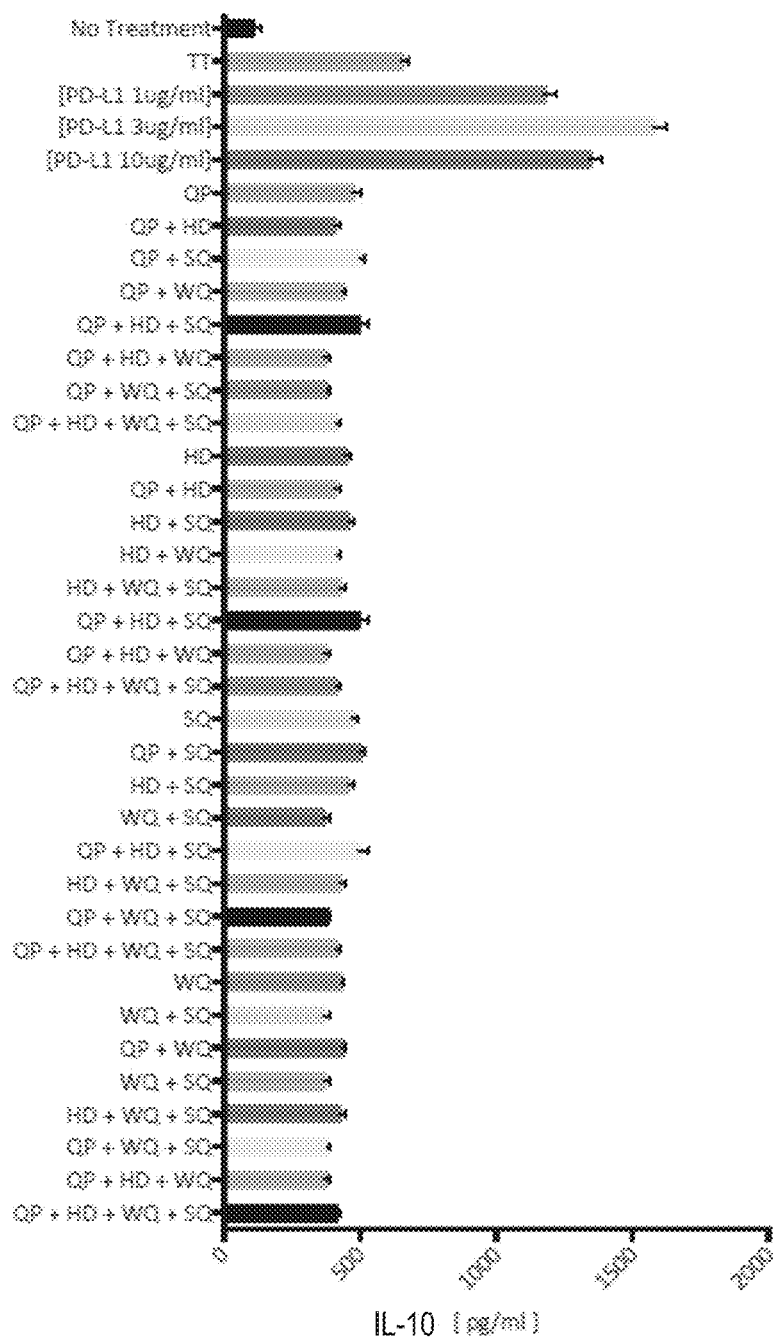
FIG. 19. Graph showing IL-10 production by PBMCs in a tetanus toxoid recall assay, after stimulation with various combinations of peptides QP20, HD20, WQ20, and SQ20.
Figure 20:
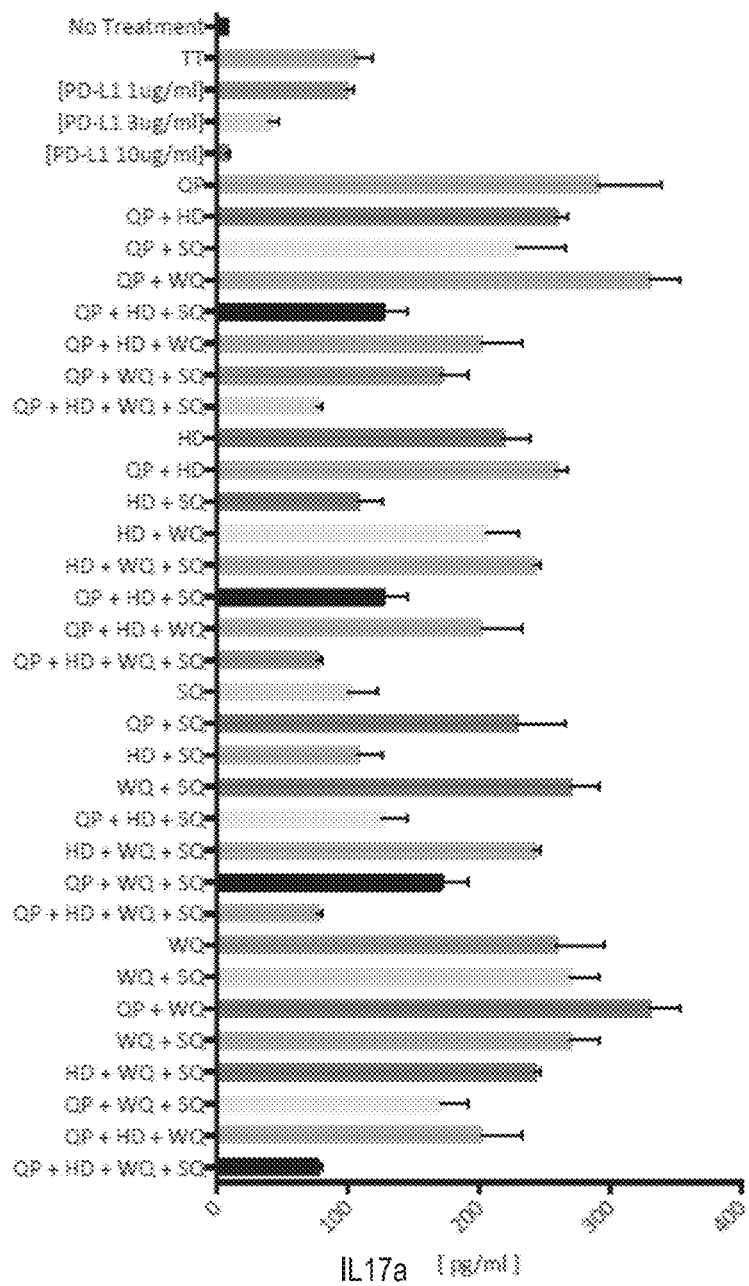
FIG. 20. Graph showing IL-17a production by PBMCs after stimulation with various combinations of peptides QP20, HD20, WQ20, and SQ20.
Figure 21:
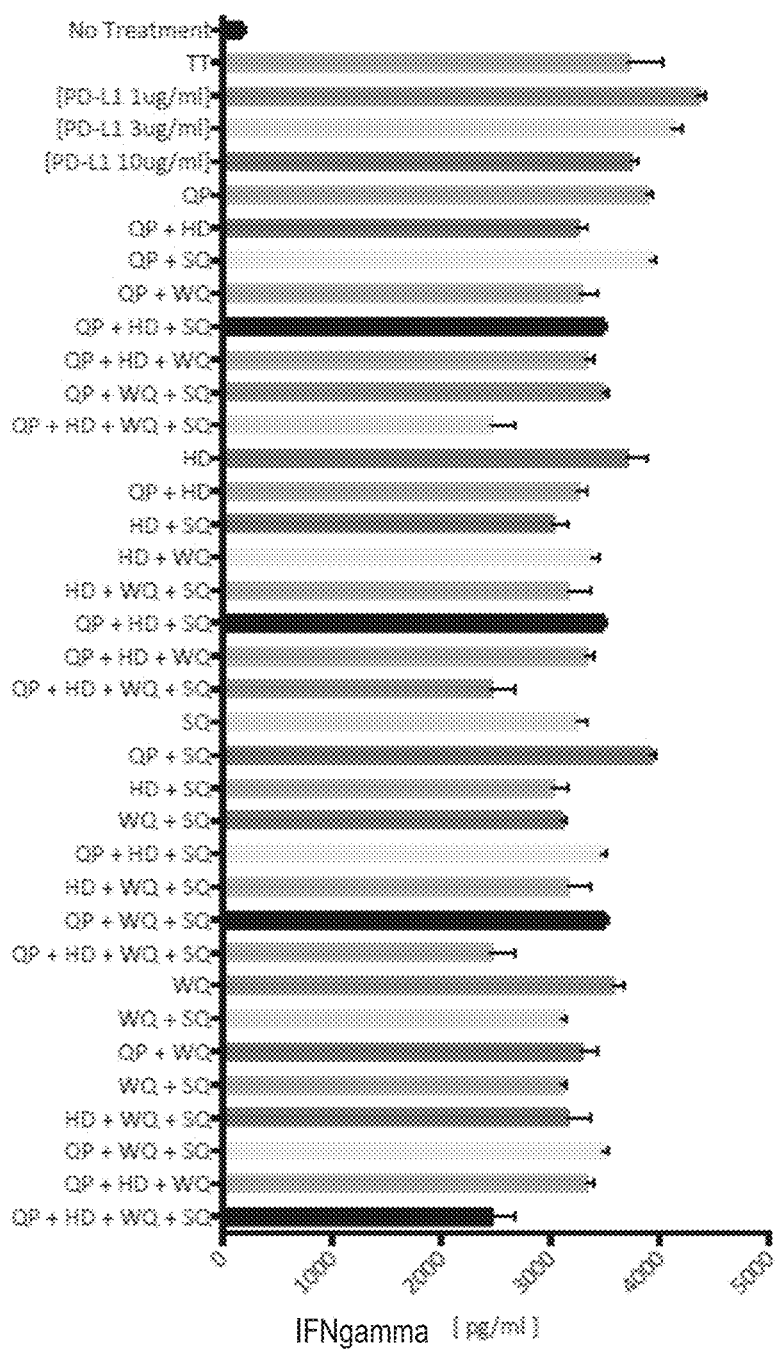
FIG. 21. Graph showing IFNγ production by PBMCs after culture with various combinations of peptides QP20, HD20, WQ20, and SQ20.
Figure 22:
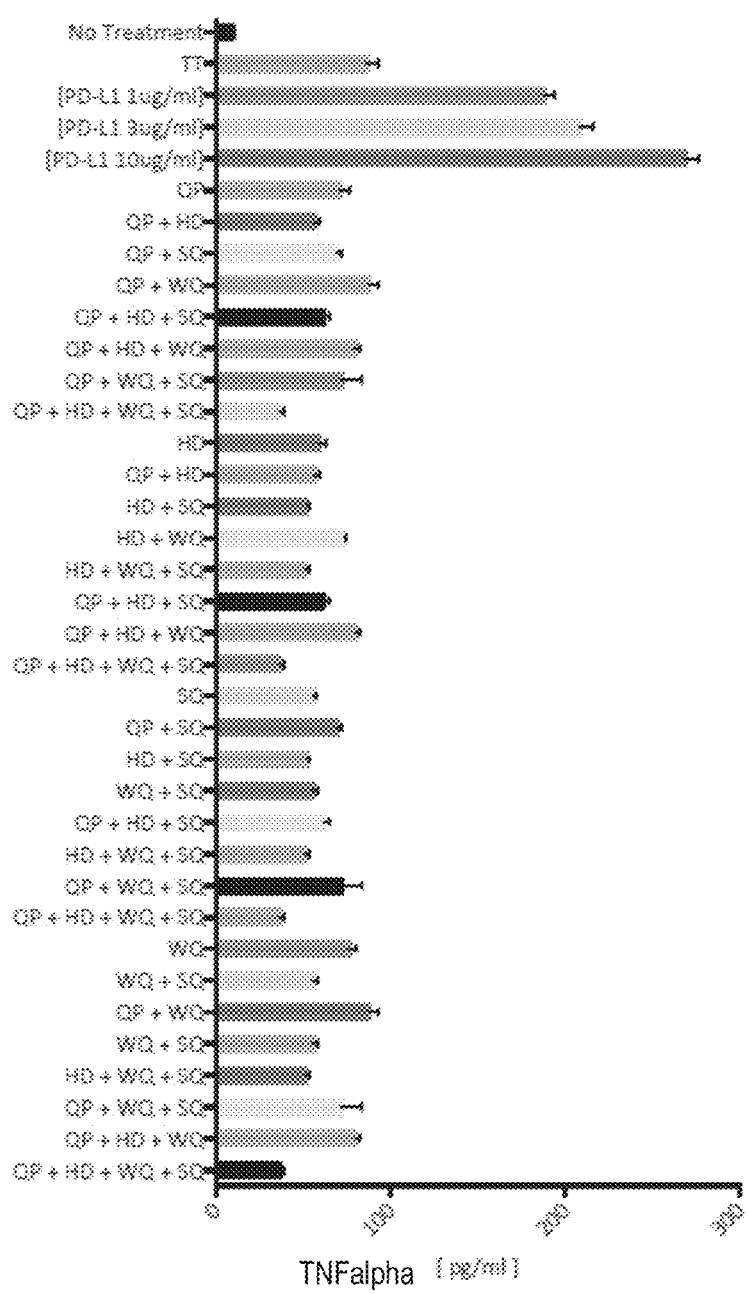
FIG. 22. Graph showing TNFα production by PBMCs after culture with various combinations of peptides QP20, HD20, WQ20, and SQ20.
Figure 23A:
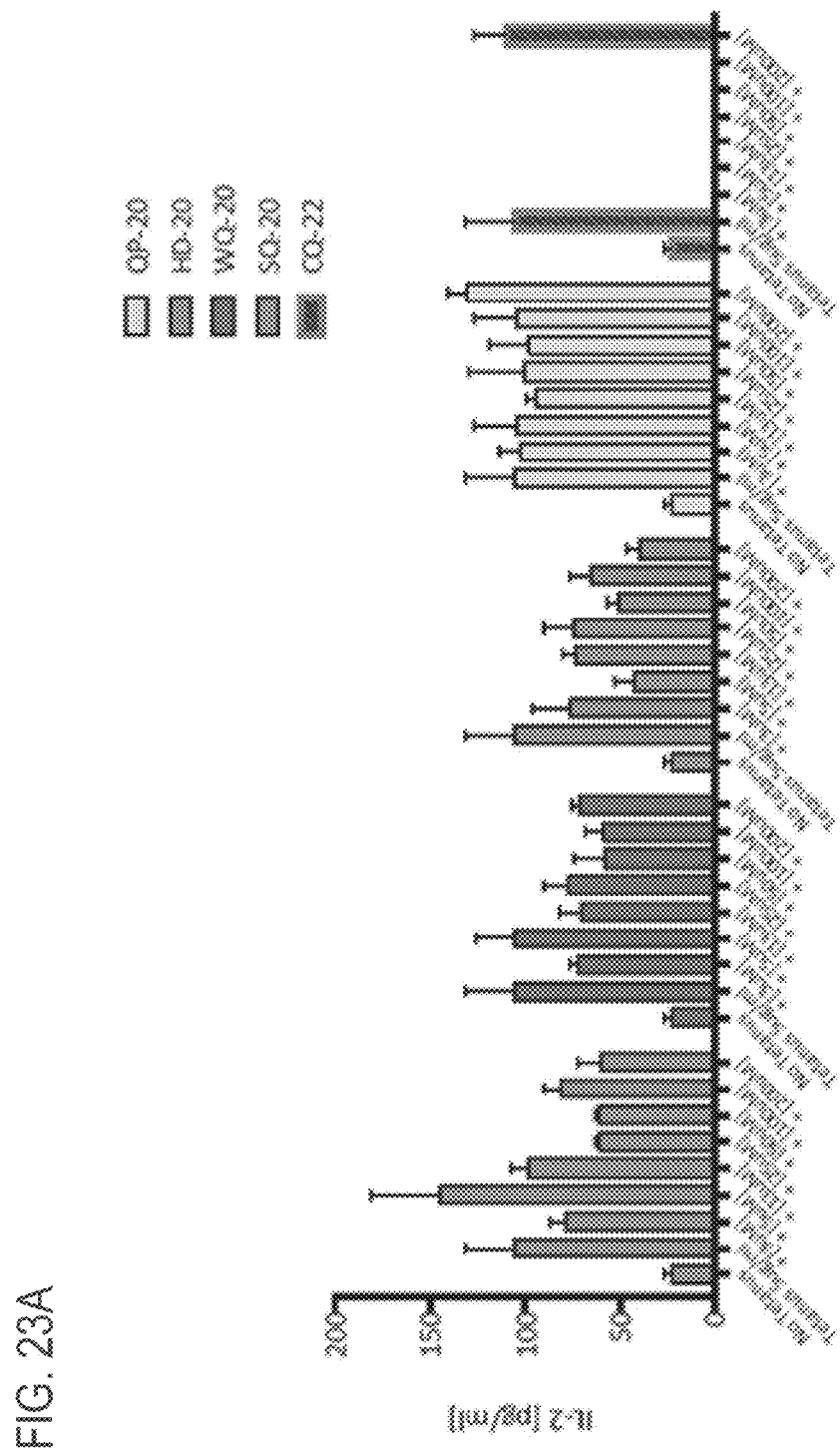
FIG. 23A. Graph showing IL-2 production by PBMCs from donor A after culture with peptides QP20, HD20, WQ20, and SQ20, or CQ-22.
Figure 23B:
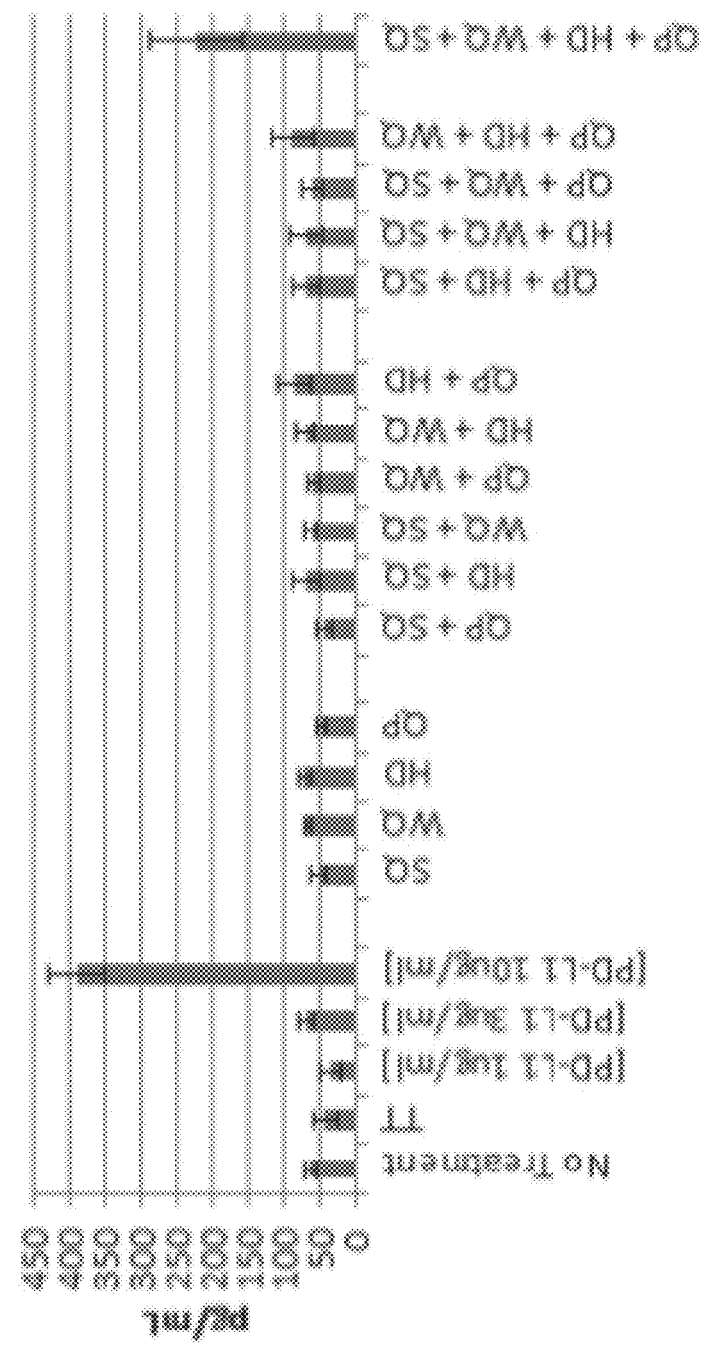
FIG. 23B. Graph showing IL-2 production by PBMCs from donor B after culture with peptides QP20, HD20, WQ20, or SQ20 and combinations of these peptides.
Figure 24A:
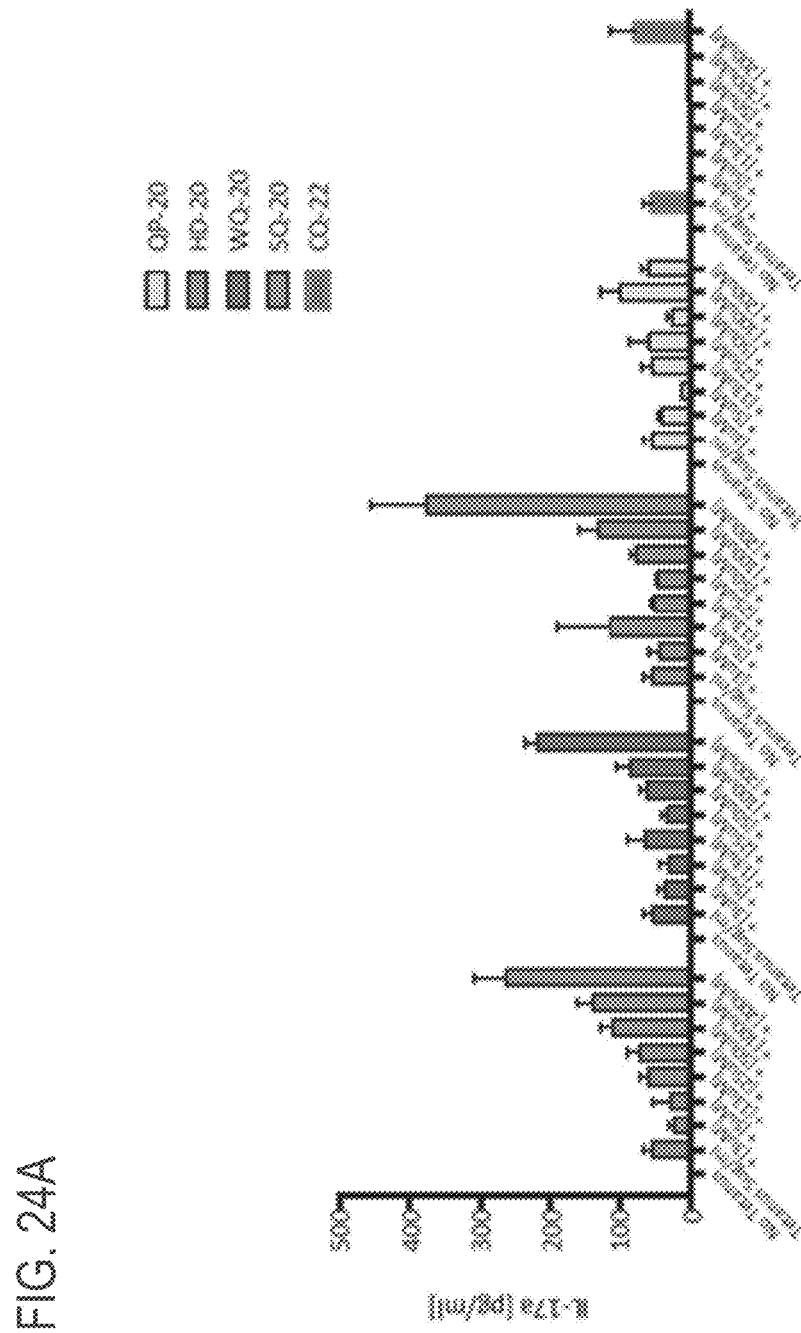
FIG. 24A. Graph showing IL-17a production by PBMCs from donor A after culture with peptides QP20, HD20, WQ20, and SQ20, or CQ-22.
Figure 24B:
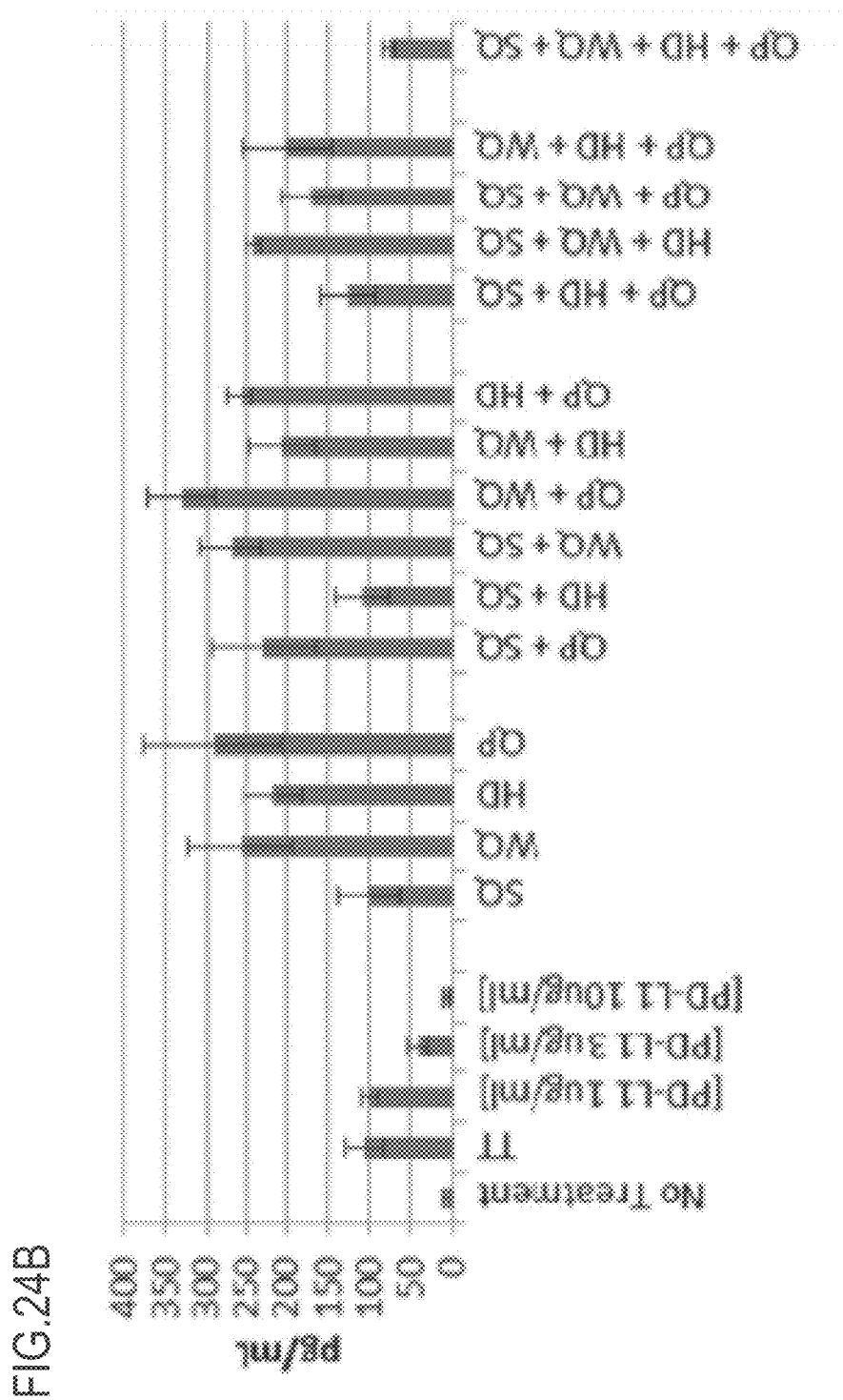
FIG. 24B. Graph showing IL-17a production by PBMCs from donor B after culture with peptides QP20, HD20, WQ20, or SQ20 and combinations of these peptides.

The results of assays of the peptides identified above are shown in FIGS. 8A-B. These results demonstrate that each of the four peptides restores luciferase expression in a dose-dependent manner, with peak-fold inhibition of approximately 1.5 at a concentration of approximately 25 μM.

Example 4. Tetanus Toxoid Recall Assay Using Individual Peptides

Peptides 1-4 were tested in a human PBMC-based tetanus antigen recall assay. "Peptide CQ-22" was used as a negative control.

PBMCs were obtained from plasma of human donors and tested in vitro for recall of tetanus toxoid. Suitable PBMCs were cryopreserved until needed, then thawed and cultured in a 96-wellplate. Tetanus toxoid was added to the cultures in the presence or absence of peptides 1-4, and the production of cytokines and cell surface T cell activation markers were examined.

The results of these assays are shown in FIGS. 9-15 and summarized qualitatively in Table 2. In the table, "x" indicates no effect, "−" indicates a possible low effect, "+" indicates some effect, and "++" indicates a definite effect.

TABLE 2

| peptide | IL-2 | IL-4 | IL-6 | IL-10 | IL-17a | IFNγ | TNFα |
|---------|------|------|------|-------|--------|------|------|
| QP20 | x | − | x | x | x | x | x |
| HD20 | − | x | ++ | x | ++ | ++ | ++ |
| WQ20 | − | ++ | ++ | x | ++ | ++ | ++ |
| SQ20 | + | − | ++ | + | ++ | ++ | + |

The results demonstrated a trend towards modest enhancement of IL-6, IL-17α, IFNγ, and TNFα production at the highest concentrations of peptides. No significant enhancement of IL-2 production was detected.

Example 5. Tetanus Toxoid Recall Assay Using Combinations of Peptides

Combinations of peptides were tested in the antigen recall assay described above, using a different PBMC donor and a different lot number of tetanus toxoid. The results are shown in FIGS. 16, 17, 18, 19, 20, 21, and 22. These results demonstrated that the combination of the four peptides combination of the four peptides QP20, HD20, WQ20, and SQ20 result in increased IL-2 production and reduced IL-17a production.

The effect of peptides QP20, HD20, WQ20, and QP20 on the production of IL-2 and IL-17a appears to be donor-specific, as shown in FIGS. 23A-B and 24A-B.

Example 6. BIACORE® Assays

BIACORE® assays were carried out using a BIACORE® T-200 at 25° C. The assay and regeneration buffers contained 10 mM HEPES (pH 7.4), 150 mM NaCl, 3 mM EDTA, and 0.05% P20. The immobilization buffer was 10 mM sodium acetate, pH 5.0. The flow rate used for immobilizing the ligand was 5 μl/min. The flow rate for kinetics analysis was 30 μl/min.

Scouting.

12,000 response units (RU) of human and 6000 RU of mouse PD-1 receptors were directly immobilized on flow cell 2 and flow cell 4 of the CMS chip by amine coupling method (EDC/NHS). The un-occupied sites were blocked with 1M ethanol amine. Scouting was performed at a single analyte concentration of 25 μM to confirm yes/no binding. Flow cell 1 was kept blank and used for reference subtraction. Binding of analyte to the ligand was monitored in real time.

Full Kinetics.

Based on the scouting results, full kinetics were performed by immobilizing higher RU of the ligand to a new chip and analyte concentration at 25 μM, followed by serial dilution to 12.5, 6.25, 3.125, 1.562, 0.78 and 0 μM concentration or as indicated. Due to fast on rate and off rate, KD was determined by steady state equilibrium kinetics.

Chi square ($\chi^2$) analysis was carried out between the actual sensorgram and a sensorgram generated from the BIANALYSIS® software (black line) to determine the accuracy of the analysis. A $\chi^2$ value within 1-2 is considered significant (accurate) and below 1 is highly significant (highly accurate). The results are summarized in Table 3.

TABLE 3

| Ligand 10,000 RU | Analyte | Rmax (RU) | KA(1/M) | KD (M) | Conc. (μM) | $\chi^2$ |
|---|---|---|---|---|---|---|
| mouse PD-1 | WQ-21 | 270 | $1.31 \times 10^3$ | $7.61 \times 10^{-4}$ | 0-25 | 0.0203 |

TABLE 3-continued

| Ligand 10,000 RU | Analyte | Rmax (RU) | KA(1/M) | KD (M) | Conc. (μM) | $\chi^2$ |
|---|---|---|---|---|---|---|
| mouse PD-1 | QP-20 | 13.4 | $1.80 \times 10^4$ | $5.54 \times 10^{-5}$ | 0-25 | 0.0446 |
| mouse PD-1 | HD-20 | 76 | $4.25 \times 10^3$ | $2.35 \times 10^{-4}$ | 0-25 | 0.11 |
| mouse PD-1 | SQ-20 | 12.8 | $2.14 \times 10^4$ | $4.68 \times 10^{-5}$ | 0-25 | 0.039 |
| human PD-1 | WQ-21 | 84.7 | $3.28 \times 10^3$ | $3.05 \times 10^{-4}$ | 0-25 | 0.0309 |
| human PD-1 | QP-20 | 3.83 | $9.36 \times 10^4$ | $1.07 \times 10^{-5}$ | 0-25 | 0.0569 |
| human PD-1 | HD-20 | 3.35 | $3.18 \times 10^5$ | $3.41 \times 10^{-6}$ | 0-12.5 | 0.0733 |
| human PD-1 | SQ-20 | 4.05 | $1.94 \times 10^5$ | $5.16 \times 10^{-6}$ | 0-25 | 0.111 |
| mouse PD-1 | Mouse PD-L1 | 259 | $2.75 \times 10^6$ | $3.64 \times 10^{-7}$ | 0-50 | 0.105 |
| human PD-1 | Human PD-L1 | 213 | $6.92 \times 10^6$ | $1.44 \times 10^{-7}$ | 0-50 | 2.44 |

These results indicate that each of the four peptides bind both human and mouse PD-1. QP20 and SQ20 showed the highest affinity towards mouse PD-1. HD20 and SQ20 showed the highest affinity towards human PD-1.

Example 7. Experimental Metastasis Model

Efficacy of the peptides was evaluated in a B16-F10-LacZ experimental metastasis model. In this model, B16-F10-LacZ cells, transfected to express the LacZ gene that encodes β-galactoside, an intracellular enzyme, are injected into the tail vein of syngeneic mice. The cells travel through the circulation, settle in the lungs, and form tumors. Mice are terminated 2 weeks after implant. When the enzyme cleaves its substrate, X-gal, the products dimerize and change color and can be detected ex vivo. The number of metastatic tumors on the surface of the lung is then quantified by manual counting of tumors under a dissecting microscope.

Briefly, mice (N=7) were implanted on study day 0 with B16-F10-LacZ tumor cells ($5 \times 10^5$ or $1 \times 10^6$ cells per mouse) by intravenous injection in the tail vein. Mice received a treatment of the peptide combination (200 μg, 20 μg, or 2 μg, each peptide per dose) intravenously by tail vein injection on study days 2, 5, 7, 9 and 12. Detailed clinical examinations and body weights were recorded regularly during treatment. Mice were terminated on study day 14, and their lungs were removed and stained. The number of tumor metastases were counted. Treatment groups are described in Table 4.

TABLE 4

| Group | N | Implant | Treatment | Dose | Route | Treatment Days |
|---|---|---|---|---|---|---|
| 1 | 7 | $5 \times 10^5$ | QP-20, SQ-20, HD-20, WQ-20 | 200 μg | IV | SD 2, 5, 7, 9, 12 |
| 2 | 7 | $5 \times 10^5$ | QP-20, SQ-20, HD-20, WQ-20 | 20 μg | IV | SD 2, 5, 7, 9, 12 |
| 3 | 7 | $5 \times 10^5$ | QP-20, SQ-20, HD-20, WQ-20 | 2 μg | IV | SD 2, 5, 7, 9, 12 |
| 4 | 7 | $5 \times 10^5$ | Untreated | — | — | — |
| 5 | 7 | $1 \times 10^6$ | QP-20, SQ-20, HD-20, WQ-20 | 200 μg | IV | SD 2, 5, 7, 9, 12 |
| 6 | 7 | $1 \times 10^6$ | Untreated | — | — | — |

Figure 25:
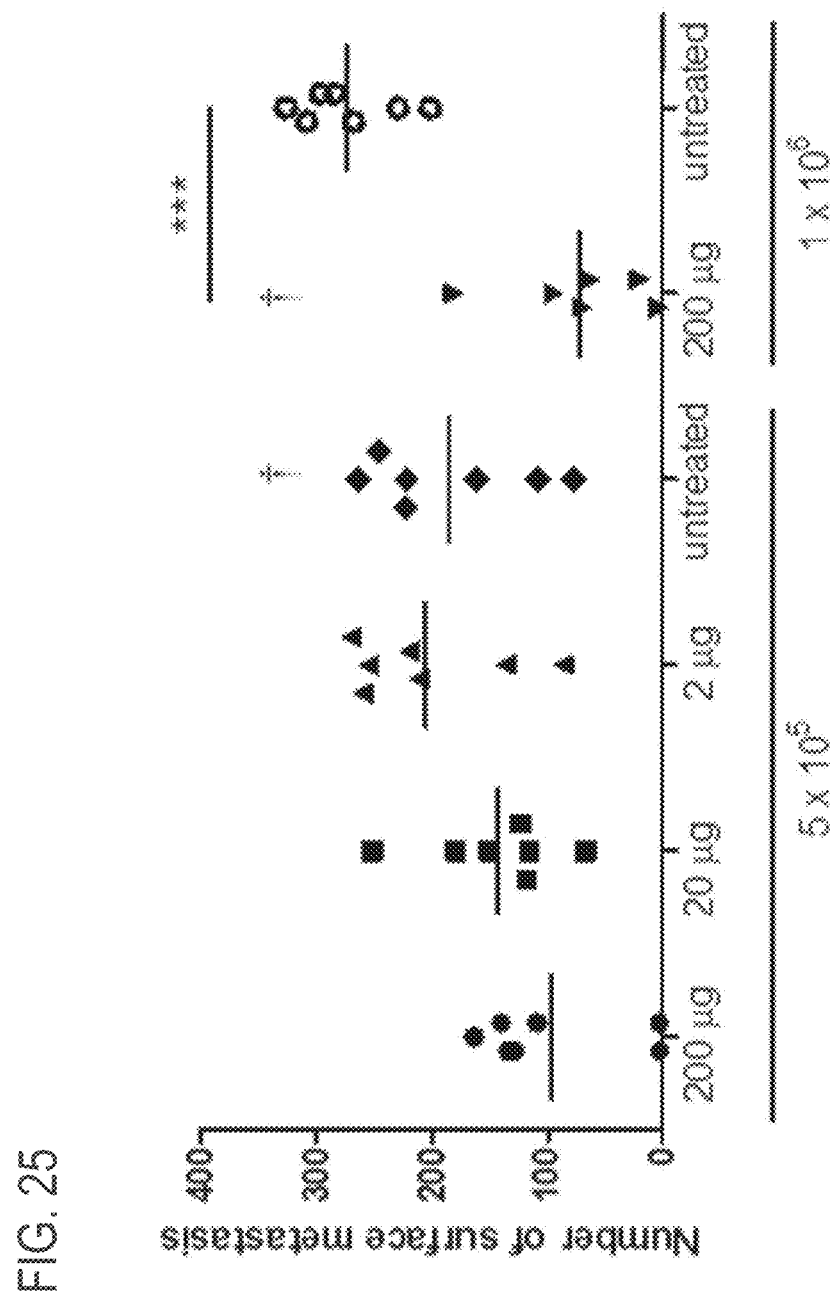
FIG. 25. Graph showing number of surface metastases in mice bearing B16-F10-LacZ tumor cells and treated with combinations of peptides.

The results are shown in FIG. 25. A good dose response was observed when mice were implanted at both cell concentrations. Mice treated with the highest dose of peptide mixture (200 μg) had the fewest tumors (average 97), and mice treated with the lowest dose of peptide mixture (2 μg) had the most tumors (average 205). Similarly, in the two groups that were implanted with high tumor numbers, the untreated group had significantly more tumors. This indicates that the 4 peptides in combination showed a dose-dependent efficacy on B16-F10-LacZ tumor growth in vivo. Moreover, the peptide combination was well tolerated by the mice and did not have any acute adverse effects on animal health.

Example 8. Effect of Peptide Combination on the Immunogenicity of a Malaria Vaccine Immunogenicity of the peptide combination as a prophylactic vaccine adjuvant was assessed in a mouse model of malaria. Balb/c mice immunized with an adenovirus-based malaria vaccine expressing the *Plasmodium yoelii* circumsporozoite protein (AdPyCS) were given 200 μg of the peptide combination, anti-PD-1 mAb, anti-PDL1 mAb, or the negative control peptide ovalbumin (OVA) on days 1, 3, 5, and 7 after immunization with AdPyCS (Table 5). Note that no additional adjuvant was added to the AdPyCS antigen. Spleens were collected 12 days after immunization, and the number of splenic PyCS-specific, IFNγ-secreting CD8+ T cells was determined via ELISpot assay. Note that for the ELISpot assay, splenocytes were stimulated with the SYVPSAEQI peptide (SEQ ID NO:5), an H-2Kd-restricted CD8+ T cell epitope of PyCS.

TABLE 5

| Cohort | Test Sample | # Mice | Route | Treatment days |
|---|---|---|---|---|
| 1 | AdPyCS only | 5 | — | — |
| 2 | AdPyCS + control OVA peptide (200 μg) | 5 | i.p. | 0, 1, 3, 5, 7 |
| 3 | AdPyCS + peptide combo (200 μg) | 5 | i.p. | 0, 1, 3, 5, 7 |
| 4 | AdPyCS + anti-PD-1 antibody (200 μg) | 5 | i.p. | 0, 1, 3, 5, 7 |
| 5 | AdPyCS + anti-PDL1 antibody (200 μg) | 5 | i.p. | 0, 1, 3, 5, 7 |

Significant differences in the average number±standard deviation of CSP-specific, IFNγ-secreting CD8+ T cells per $0.5 \times 10^6$ splenocytes between the AdPyCS alone (Cohort 1) and the peptide combination (Cohort 3), anti-PD-1 antibody (Cohort 4) or anti-PD-L1 antibody (Cohort 5) were detected using the one-way ANOVA test (*** $p<0.001$, and * $p<0.05$). These results demonstrate that the peptide combination (Cohort 3) is functionally active in vivo, increasing the number of CSP-specific, IFNγ-secreting CD8+ T cells ~1.6-fold relative to AdPyCS alone (Cohort 1), which was similar to changes with anti-PD-1 or -PD-L1 antibody (Cohort 4 and 5).

Example 9. Effect of Peptide Combination on Survival in a Model of Sepsis

Sepsis can negatively alter T cell function and survival, however this can be reversed when the PD-1:PDL1 interaction is blocked, which results in improved survival. Thus the efficacy of the peptide combination was assessed in a representative, clinically relevant model of sepsis where CD1 mice are subjected to cecal ligation and puncture (CLP) to induce intra-abdominal peritonitis. For this study, 200 μg of either the peptide combination or anti-PD-1 antibody were administered i.v. at 2, 24, 48, 72 and 96 hours after surgery. A vehicle control group was also included. Six mice were in each group. All mice were checked twice daily for signs of morbidity and mortality. Administration of the peptide combination conferred an enhanced survival advantage over the vehicle control group where the peptide combination showed a 2-fold higher survival rate (Table 6). Moreover, survival in the peptide combination group was slightly above treatment with anti-PD-1 antibody.

TABLE 6

| Group | % Survival |
| --- | --- |
| Vehicle Control | 50% |
| Anti-PD-1 antibody | 83% |
| PD-1 Peptide Combo | 100% |

Example 10. Effect of Peptide Combination on Serum HBsAg Levels in HBV-Infected Mice The combination of QP20, HD20, WQ20, and SQ20 peptides was assessed in a hepatitis B virus (HBV) mouse model where the role of PD-1 in T cell exhaustion and immunotolerance is documented (Tzeng et al., 2012; Ye et al., 2015). PD-1 is elevated in the hepatic T cells of mice with persistent HBV infection but not in animals that have cleared the infection. In this model, it has been shown that inhibition of the PD-1/PD-L1 interaction with an anti-PD-1 mAb both increases antigen-specific IFNγ production by hepatic T cells and reverses HBV persistence (Tzeng et al., 2012). This mouse model of persistent HBV presented an opportunity to test whether the combination of QP20, HD20, WQ20, and SQ20 peptides can reverse T cell exhaustion in vivo and aid the immune system in controlling viral infection.

Mice infected with HBV were treated with saline (negative control), 200 μg of QP20, HD20, WQ20, and SQ20 peptides combined, or 200 μg anti-PD-1 mAb at 9 time points, 2 days prior to infection and days 1, 3, 6, 9, 12, 14, 17 and 20 post infection. The level of serum HB surface antigen (HBsAg) was monitored by ELISA on days 7, 14, and 21 to follow the infection (higher levels of serum HBsAg are reflective of higher viral titer) and detect the immune enhancement activity of the combination of QP20, HD20, WQ20, and SQ20 peptides. The group treated with the combination of QP20, HD20, WQ20, and SQ20 peptides showed significantly lower mean level of serum HBsAg at weeks 2 and 3 post infection ($p<0.05$, 1-way ANOVA, Tukey's Multiple Comparison Test) compared to the saline negative control.

REFERENCES

Kontermann, "Half-life extended biotherapeutics," Expert Opin. Biol. Ther. 16, 903-15, 2016.
Penchala et al., "A biomimetic approach for enhancing the in vivo half-life of peptides," Nat. Chem. Biol. 11, 793-98, 2015.
Tzeng et al., "PD-1 blockage reverses immune dysfunction and hepatitis B viral persistence in a mouse animal model," PLoS One 7(6):e39179, 2012.
Ye et al., "T-cell exhaustion in chronic hepatitis B infection: current knowledge and clinical significance," Cell Death Dis. March 19; 6:e1694, 2015.
Zorzi et al., "Acylated heptapeptide binds albumin with high affinity and application as tag furnishes long-acting peptides," Nature Communications 8, 16092, 2017.

The invention claimed is:

1. A method of inhibiting progression of a hyperproliferative disorder, comprising administering to a patient in need thereof an effective amount of a pharmaceutical composition comprising:
   (a) up to four peptides selected from the group consisting of:
      (i) a peptide consisting of the amino acid sequence SEQ ID NO:1;
      (ii) a peptide consisting of the amino acid sequence SEQ ID NO:2;
      (iii) a peptide consisting of the amino acid sequence SEQ ID NO:3; and
      (iv) a peptide consisting of the amino acid sequence SEQ ID NO:4; and
   (b) a pharmaceutically acceptable vehicle.

2. The method of claim 1, wherein the hyperproliferative disorder is a cancer.

3. The method of claim 2, wherein the cancer is a melanoma.

4. The method of claim 2, further comprising administering a cancer vaccine to the patient.

5. The method of claim 1, further comprising administering a chimeric antigen receptor (CAR) T cell therapy to the patient.

6. The method of claim 1, wherein the pharmaceutical composition comprises only one of the four peptides.

7. The method of claim 1, wherein the pharmaceutical composition comprises only two of the four peptides.

8. The method of claim 6, wherein the pharmaceutical composition comprises only three of the four peptides.

9. The method of claim 6, wherein the pharmaceutical composition comprises all four of the peptides.

10. The method of claim 7, wherein the two peptides are the peptide consisting of the amino acid sequence SEQ ID NO:1 and the peptide consisting of the amino acid sequence SEQ ID NO:2.

11. The method of claim 7, wherein the two peptides are the peptide consisting of the amino acid sequence SEQ ID NO:1 and the peptide consisting of the amino acid sequence SEQ ID NO:3.

12. The method of claim 7, wherein the two peptides are the peptide consisting of the amino acid sequence SEQ ID NO:1 and the peptide consisting of the amino acid sequence SEQ ID NO:4.

13. The method of claim 7, wherein the two peptides are the peptide consisting of the amino acid sequence SEQ ID NO:2 and the peptide consisting of the amino acid sequence SEQ ID NO:3.

14. The method of claim 7, wherein the two peptides are the peptide consisting of the amino acid sequence SEQ ID NO:2 and the peptide consisting of the amino acid sequence SEQ ID NO:4.

15. The method of claim 7, wherein the two peptides are the peptide consisting of the amino acid sequence SEQ ID NO:3 and the peptide consisting of the amino acid sequence SEQ ID NO:4.

16. The method of claim 8, wherein the three peptides are the peptide consisting of the amino acid sequence SEQ ID NO:1, the peptide consisting of the amino acid sequence SEQ ID NO:2, and the peptide consisting of the amino acid sequence SEQ ID NO:3.

17. The method of claim 8, wherein the three peptides are the peptide consisting of the amino acid sequence SEQ ID NO:1, the peptide consisting of the amino acid sequence SEQ ID NO:2, and the peptide consisting of the amino acid sequence SEQ ID NO:4.

18. The method of claim 8, wherein the three peptides are the peptide consisting of the amino acid sequence SEQ ID NO:2, the peptide consisting of the amino acid sequence SEQ ID NO:3, and the peptide consisting of the amino acid sequence SEQ ID NO:4.

19. The method of claim 8, wherein the three peptides are the peptide consisting of the amino acid sequence SEQ ID NO:1, the peptide consisting of the amino acid sequence SEQ ID NO:3, and the peptide consisting of the amino acid sequence SEQ ID NO:4.

* * * * *